(12) United States Patent
Stehman-Breen et al.

(10) Patent No.: US 11,491,222 B2
(45) Date of Patent: *Nov. 8, 2022

(54) METHOD OF TREATING LOWER BACK PAIN

(71) Applicant: REGENERON PHARMACEUTICALS, INC., Tarrytown, NY (US)

(72) Inventors: Catherine Stehman-Breen, York, ME (US); John Davis, Scarsdale, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 143 days.

This patent is subject to a terminal disclaimer.

(21) Appl. No.: 16/920,178

(22) Filed: Jul. 2, 2020

(65) Prior Publication Data

US 2021/0060159 A1   Mar. 4, 2021

Related U.S. Application Data

(63) Continuation of application No. 15/824,106, filed on Nov. 28, 2017, now Pat. No. 10,736,961.

(60) Provisional application No. 62/427,365, filed on Nov. 29, 2016.

(51) Int. Cl.
    *A61K 39/395* (2006.01)
    *C07K 16/22* (2006.01)
    *A61K 39/00* (2006.01)

(52) U.S. Cl.
    CPC .... *A61K 39/3955* (2013.01); *A61K 39/39541* (2013.01); *C07K 16/22* (2013.01); *A61K 2039/505* (2013.01); *A61K 2039/545* (2013.01); *C07K 2317/565* (2013.01); *C07K 2317/76* (2013.01); *C07K 2317/92* (2013.01)

(58) Field of Classification Search
    None
    See application file for complete search history.

(56) References Cited

PUBLICATIONS

Younger et al. (Current Pain and Headache Reports 13: 39-43, 2009).*
Dakin et al. (Ann Rheum Dis. 80: 509-517, 2021).*
Chang et al., "Anti-nerve growth factor in pain management: current evidence" Journal of Pain Research (2016) 9:373-383.
Kivitz et al., "Efficacy and safety of tanezumab versus naproxen in the treatment of chronic low back pain" Pain (2013) 154:1009-1021.
Tiseo et al., "Fasinumab (REGN475), an antinerve growth factor monoclonal antibody, for the treatment of acute siatic pain: results of a proof-of-concept study" Journal of Pain Research (2014) 7:523-530.
Tiseo et al., "Fasinumab (REGN475), an antibody against nerve growth factor for the treatment of pain: Results from a double-blind, placebo-controlled exploratory study in osteoarthritis of the knee" Pain (2014) 155:1245-1252.
Rosenblum et al. "Opioids and the Treatment of Chronic Pain: Controversies, Current Status and Future Directions" Exp Clin Psychopharmacol. Oct. 2008; 16(5): 405-416: doi:10.1037/a0013628.
ClinicalTrials.gov archive, History of Changes for Study: NCT02620020, Submitted Date: Nov. 16, 2016 (v4), https://clinicaltrials.gov/ct2/history/NCT02620020?V_4=View#StudyPageTop.

* cited by examiner

*Primary Examiner* — Christine J Saoud
(74) *Attorney, Agent, or Firm* — Karl Bozicevic; Bozicevic, Field & Francis LLP

(57) ABSTRACT

A method of treating a patient suffering from low back by administering to the patient a pharmaceutical composition comprising a therapeutically effective amount of an antibody that binds specifically to nerve growth factor (NGF) or an antigen binding fragment thereof.

12 Claims, 10 Drawing Sheets

Specification includes a Sequence Listing.

Schedule of Events – Screening Period Through Week 16

| | Screening Period | Pre-Randomization Period | | Treatment | | | | | End of Treatment Period | Treatment Period Early Termination Visit |
|---|---|---|---|---|---|---|---|---|---|---|
| Study Week | | | 1 Baseline | 1 | 2 | 4 | 8 | 12 | 16 | |
| Study Day (visit window) | up to -37 to -8 | -7 (+3) Pre-Rand Visit | 1 | 8 (±1) | 15 (±3) | 29 (±7) | 57 (±7) | 85 (±7) | 113 (±7) | ET |
| Visit Number | 1 | 2 | 3 | Ph call 1 | 4 | 5 | 6 | 7 | 8 | ET |
| Screening/Baseline: | | | | | | | | | | |
| Informed Consent | X | | | | | | | | | |
| Inclusion/Exclusion | X | X | X | | | | | | | |
| Genomics sub-study informed consent[1] | X | | | | | | | | | |
| Medical History | X | | | | | | | | | |
| Medication History | X | | | | | | | | | |
| Demographics | X | | | | | | | | | |
| Height | X | | | | | | | | | |
| Bilateral radiograph of knees, hips and shoulders[2] | X | | | | | | | | | |
| Lumbar spine MRI[3] | X | | | | | | | | | |
| MRI of any knee or hip with baseline K-L ≥3[2] | X | | | | | | | | X | X[4] |
| NRS/EDiary training[5] | | X | | | | | | | | |
| Assessment of peripheral or central pain | X | | | | | | | | | |
| painDETECT Questionnaire | X | | | | | | | | | |
| Randomization | | | X | | | | | | | |
| Treatment: | | | | | | | | | | |
| SC Study Drug Injection[6] | | | LOADING DOSE | | | X | X | X | | |
| IV Study Drug Infusion[6] | | | X | | | | X | | | |

FIG. 1A

| Schedule of Events – Screening Period Through Week 16 | | | | | | | | | |
|---|---|---|---|---|---|---|---|---|---|
| Dispense paracetamol/acetaminophen | | X | | | | | | | |
| Paracetamol/acetaminophen accountability | | | X | X | X | X | X | X | X |
| Concomitant medications | X | X | X | X | X | X | X | X | X |
| Efficacy: | | | | | | | | | |
| LBPI NRS[7] | X | X | X | X | X | X | X | X | X |
| Roland Morris Disability Questionnaire | | | X | X | X | X | X | X | X |
| Patient Global Assessment LBP | X | | X | X | X | X | X | X | X |
| MOS Sleep Scale Survey | | | X | X | X | | X | X | X |
| SF-36 | | | X | X | X | | X | X | X |
| EQ-5D-5L | | | X | X | X | | X | X | X |
| Safety: | | | | | | | | | |
| Weight | X | | | | | | X | X | X |
| Vital Signs[8] | X | | X | X | X | X | X | X | X |
| Physical Examination[9] | X | | | | | | | X | X |
| Electrocardiogram | X | | | | | | | X | X |
| Joint Pain Questionnaire | X | | X | | X | X | | | |
| Event-triggered imaging[10] | | | | | | | | | |
| Orthostatic blood pressure | X | | X | | X | X | X | X | X |
| Survey of autonomic symptoms | X | | X | | X | X | X | X | X |
| Neurologic examination | FULL | | BRIEF | BRIEF | BRIEF | BRIEF | BRIEF | FULL | FULL |
| Adverse Events | X | X | X | X | X | X | X | X | X |
| Pre-op questionnaire (TJR)[11] | | | | | | | | | X |
| Laboratory Testing:[6] | | | | | | | | | |
| Hematology | X | | X | | X | X | X | X | X |
| Blood Chemistry | X | | X | | X | X | X | X | X |
| HbA1c | X | | | | | | | | |
| FSH and estradiol[12] | X | | | | | | | | |
| Pregnancy test (WOCBP)[13] | SERUM | | URINE | URINE | URINE | URINE | URINE | SERUM | SERUM |

FIG. 1B

Schedule of Events–Screening Period Through Week 16

| Urinalysis | X | | | | | X | | X |
|---|---|---|---|---|---|---|---|---|
| PK/Drug Concentration and ADA Samples:6 | | | | | | | | |
| PK/Drug conc. sample | | X | | X | X | X | X | X |
| ADA sample | | X | | X | | X | X | X |
| Genomics sub - study sample1 | | X | | | | | | |
| Research serum/plasma sample | | X | | X | X | X | X | X |

1. Only for patients who provide written informed consent for the optional genomics sub-study. The sample should be collected at the baseline visit, but may be collected at any subsequent visit during the study.
2. If screening radiographs are inconclusive for potential joint-related findings, an MRI of the knee, hip, or shoulder should be performed. After the patient has otherwise met study eligibility criteria assessed during the screening period, an MRI of any knee or hip joint that has a baseline K-L score of ≥3 will be performed prior to the pre-randomization visit. Confirmation that the image has been accepted and confirmed query-free by the central reader must be received by the site before the pre-randomization visit. Confirmation from the central reader that there are no exclusionary findings on MRI must be received from the central reader before a patient can be randomized.
3. A lumbar spine AP/Lateral should be obtained if the MRI of the lumbar spine shows evidence suggestive of a destructive or unstable process.
4. Early Termination: Imaging assessments (X-rays of the knees, hips, and shoulders, and MRI) need to be repeated only if it has been >30 days since the joint was last imaged. If it has been ≤30 days since imaging assessments were completed, imaging assessments may be completed at the discretion of the investigator.
5. Patients will be trained on using the EDiary after initial patient eligibility has been confirmed during the screening period. Patients will use the EDiary to report their daily NRS LBP score and daily use of paracetamol/acetaminophen through the week 16 visit.
6. Study drug administration will be the last procedure at each dosing visit, and will be done after all laboratory samples have been collected and all study assessments and procedures are performed including blood draws for drug concentration and ADA. At the day 1 and week 8 visits, patients will receive the SC injection first, followed by the IV infusion. After IV administration of study drug, patients will be observed in the clinic for approximately 2 hours for evidence of a hypersensitivity reaction, and for 1 hour after SC dosing.
7. Low back pain intensity NRS score will be recorded into the electronic case report form (eCRF) by the site at the screening visit and at the pre-randomization visit, and by the patient each day (at approximately 6:00 PM) using the EDiary, starting during the pre-randomization period through week 16.
8. If the pulse is less than 45 bpm, an ECG with rhythm strip will be obtained and sent to the central reader to confirm the heart rate and rhythm.
9. The physical examination should include an exam of the knee, hip, and shoulder joints.
10. In addition to scheduled imaging, an X-ray and/or MRI should be considered for worsening joint pain despite treatment with analgesics, which, in the opinion of the investigator, is inconsistent with the normal progression of OA and lasts at least 2 weeks (or less at the discretion of the investigator). In cases where the joint had previously been treated with TJR surgery, an MRI is not required.

FIG. 1C

Schedule of Events–Screening Period Through Week 16

11. In the event that a patient must undergo TJR surgery during the study, the patient will complete the early termination visit and the procedures outlined in the schedule of events for TJR follow-up. The early termination visit should be completed before TJR surgery if at all possible. TJR questionnaires are Knee Society Score questionnaire for knee replacements or Harris Hip Score questionnaire for hip replacements.

12. To be performed only if postmenopausal status has to be assessed for female patients ≤59 years of age.

13. In the event of a positive urine pregnancy test result, the patient must have a serum pregnancy test with a negative result in order to continue study participation. If the serum pregnancy test is positive, the patient must be withdrawn from study drug and should be asked to return to the clinic for all remaining study visits per the visit schedule.

FIG. 1D

Schedule of Events – Follow-up Period – Week 20 through Week 36

| | Follow-up Period | | | | End of Study | Follow-up Period Early Termination |
|---|---|---|---|---|---|---|
| Study Week | Week 20 | Week 24 | Week 28 | Week 32 | Week 36 | |
| Study Day (visit window) | 141(±7) | 169(±7) | 197(±7) | 225(±7) | 253(±7) | |
| Visit Number | 9 | Ph call 2 | Ph call 3 | Ph call 4 | 10 | ET |
| Treatment: | | | | | | |
| Concomitant Meds | X | X | X | X | X | X |
| Efficacy: | | | | | | |
| LBPI NRS | X | | | | X | X |
| Roland Morris Disability Questionnaire | X | | | | X | X |
| Patient Global Assessment LBP | X | | | | X | X |
| MOS Sleep Scale Survey | X | | | | X | X |
| SF-36 | X | | | | X | X |
| EQ-5D-5L | X | | | | X | X |
| Safety: | | | | | | |
| Vital Signs[1] | X | | | | X | X |
| Physical Examination | | | | | X | X |
| Electrocardiogram | | | | | X | X |
| Joint Pain Questionnaire | X | | | | X | X |
| Orthostatic blood pressure | X | | | | X | X |
| Survey of autonomic symptoms | X | | | | X | X |
| Neurologic examination | BRIEF | | | | FULL | FULL |
| Adverse Events | X | X | X | X | X | X |
| MRI of any knee or hip with baseline K-L ≥2[2] | | | | | X | X[3] |
| Pre-op questionnaire (TJR)[3] | | | | | X | X |
| Laboratory Testing: | | | | | | |
| Hematology | | | | | X | X |
| Blood Chemistry | | | | | X | X |
| Pregnancy test (WOCBP) | URINE | | | | SERUM | SERUM |
| PK/Drug Concentration and ADA Samples: | | | | | | |
| PK/Drug conc. sample | X | | | | X | X |

FIG. 2A

| Schedule of Events – Follow-up Period – Week 20 through Week 36 | | | |
|---|---|---|---|
| ADA sample | X | X | X |
| Research serum/plasma sample | | X | X |

1. If the pulse is less than 45 bpm, an ECG with rhythm strip will be obtained and sent to the central reader to confirm the heart rate and rhythm.
2. Imaging assessments (X-rays of the knees, hips, and shoulders, and MRI) need to be repeated only if it has been >30 days since the joint was last imaged. If it has been ≤30 days since imaging assessments were completed, imaging assessments may be completed at the discretion of the investigator.
3. In the event that a patient must undergo TJR surgery during the study, the patient will complete the early termination visit and the procedures outlined in the schedule of events for TJR follow-up. The early termination visit should be completed before TJR surgery if at all possible. TJR questionnaires are Knee Society Score questionnaire for knee replacements or Harris Hip Score questionnaire for hip replacements.

FIG. 2B

Schedule of Events - Follow-up for Patients Who Undergo Total Joint Replacement Surgery

| Follow-up Study Day (Visit Window) | Follow-up Period[1] | |
|---|---|---|
| | Post-Operative<br>Follow-up Visit 1<br>4 weeks after the date of the joint replacement surgery<br>F/U Day 29 (±7) | Long-Term<br>Follow-up Visit 2<br>20 weeks after the date of the joint replacement surgery<br>F/U Day 140 (±7) |
| Treatment: | | |
| Concomitant medications | X | X |
| Safety: | | |
| Vital signs | X | X |
| Physical examination with joint exam | X[1] | X |
| Joint pain questionnaire | X | X |
| Post-operative assessment questionnaire[2] | X | X |
| Event-triggered imaging[3] | X | X |
| MRI of any knee or hip with a baseline K-L ≥3 | | X |

1. Relevant information related to the surgery should be collected, including placement of the prosthesis and healing of the surgical wound.
2. Formal post-operative assessment of joint replacements will be done by completing the Knee Society Score questionnaire for knee replacements or the Harris Hip Score questionnaire for hip replacements. Full details of these assessments are provided in the study reference manual.
3. Imaging may be performed on any joint following a report of clinically significant worsening or exacerbation of pain in that joint. In cases where the contralateral joint had previously been treated with TJR surgery, an MRI is not required.

FIG. 3

SEQUENCE LISTING

<160> NUMBER OF SEQ ID NOS: 18

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1

```
caggtgcagc tggtgcagtc tggggctgag gtgaagaagc ctggggcctc agtgaaggtc      60
tcctgcaagg tttccggatt caccctcact gaattatcca ttcactgggt gcgacaggct     120
cctggaaaag ggcttgagtg gatgggaggt tttgatcctg aagatggtga aacaatctac     180
gcacagaagt tccagggcag agtcaccatg accgaggaca tctacaga cacagcctac      240
```

```
atggagctga ccagcctgag atcggaagac acggccgtgt attactgttc aacgattttt    300
ggagtggtta ccaactttga caactggggc cagggaaccc tggtcaccgt ctcctca       357
```

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

```
Gln Val Gln Leu Val Gln Ser Gly Ala Glu Val Lys Lys Pro Gly Ala
1               5                  10                  15

Ser Val Lys Val Ser Cys Lys Val Ser Gly Phe Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ser Thr Ile Phe Gly Val Val Thr Asn Phe Asp Asn Trp Gly Gln Gly
            100                 105                 110

Thr Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcaccc tcactgaatt atcc                                            24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

```
Gly Phe Thr Leu Thr Glu Leu Ser
1               5
```

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5

```
tttgatcctg aagatggtga aaca                                            24
```

<210> SEQ ID NO 6
<211> LENGTH: 8
<212> TYPE: PRT

```
<213> ORGANISM: Artificial Sequence
<220> FEATURE:
<223> OTHER INFORMATION: synthetic

<400> SEQUENCE: 6

Phe Asp Pro Glu Asp Gly Glu Thr
1               5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
tcaacgattt ttggagtggt taccaacttt gacaac                               36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ser Thr Ile Phe Gly Val Val Thr Asn Phe Asp Asn
1               5                   10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgcaggaga cagagtcacc      60
atcacttgcc gggcaagtca ggccattaga aatgatttag ctggtatca  gcagaaacca    120 gggaaagccc ctaagcgcct gatctatgct gcattcaatt tgcaaagtgg ggtcccatca    180
agattcagcg gcagtggatc tgggacagaa ttcactctca caatcagtag cctgcagcct    240
gaagatcttg caagttatta ctgtcaacag tataatagat acccgtggac gttcggccaa    300
gggaccaagg tggaaatcaa acga                                           324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Phe Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Glu Asp Leu Ala Ser Tyr Tyr Cys Gln Gln Tyr Asn Arg Tyr Pro Trp
                    85                  90                  95

Thr Phe Gly Gln Gly Thr Lys Val Glu Ile Lys Arg
            100                 105
```

```
<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
caggccatta gaaatgat                                                       18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ala Ile Arg Asn Asp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcattc                                                                  9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Phe
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtata atagataccc gtggacg                                             27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16
```

Gln Gln Tyr Asn Arg Tyr Pro Trp Thr
1               5

<210> SEQ ID NO 17
<211> LENGTH: 847
<212> TYPE: DNA
<213> ORGANISM: Artificial Sequence
<220> FEATURE:
<223> OTHER INFORMATION: synthetic

<400> SEQUENCE: 17

```
agcgtccgga cccaataaca gttttaccaa gggagcagct ttctatcctg gccacactga      60
ggtgcatagc gtaatgtcca tgttgttcta cactctgatc acagcttttc tgatcggcat     120
acaggcggaa ccacactcag agagcaatgt ccctgcagga cacaccatcc cccaagccca     180
ctggactaaa cttcagcatt cccttgacac tgcccttcgc agagcccgca gcgcccggc      240
agcggcgata gctgcacgcg tggcggggca gacccgcaac attactgtgg accccaggct     300
gtttaaaaag cggcgactcc gttcaccccg tgtgctgttt agcacccagc ctccccgtga     360
agctgcagac actcaggatc tggacttcga ggtcggtggt gctgccccct caacaggac      420
tcacaggagc aagcggtcat catcccatcc catcttccac aggggcgaat tctcggtgtg     480
tgacagtgtc agcgtgtggg ttggggataa gaccaccgcc acagacatca agggcaagga     540
ggtgatggtg ttgggagagg tgagcattaa caacagtgta ttcaaacagt acttttttga     600
gaccaagtgc cgggacccaa atcccgttga cagcgggtgc cggggcattg actcaaagca     660
ctggaactca tattgtacca cgactcacac ctttgtcaag gcgctgacca tggatggcaa     720
gcaggctgcc tggcggttta tccggataga tacggcctgt atgtgtgtgc tcagcaggaa     780
ggctgtgaga agagcctgac ctgccgacac gctccctccc cctgcccctt ctacactctc     840
ctgggcc                                                               847
```

<210> SEQ ID NO 18
<211> LENGTH: 115
<212> TYPE: PRT
<213> ORGANISM: Artificial Sequence
<220> FEATURE:
<223> OTHER INFORMATION: synthetic

<400> SEQUENCE: 18

Ser Ser Ser His Pro Ile Phe His Arg Gly Glu Phe Ser Val Val Ser
1               5                   10                  15

Val Trp Val Gly Asp Lys Thr Thr Ala Thr Asp Ile Lys Gly Lys Glu
            20                  25                  30

Val Met Val Leu Gly Glu Val Asn Ile Asn Asn Ser Val Phe Lys Gln
        35                  40                  45

Tyr Phe Phe Glu Thr Lys Cys Arg Asp Pro Asn Pro Val Asp Ser Gly
    50                  55                  60

Cys Arg Gly Ile Asp Ser Lys His Trp Asn Ser Tyr Cys Thr Thr Thr
65                  70                  75                  80

His Thr Phe Ala Leu Thr Met Asp Gly Lys Gln Ala Ala Trp Arg Phe
                85                  90                  95

Ile Arg Ile Asp Thr Ala Cys Val Cys Val Leu Ser Arg Lys Ala Val
            100                 105                 110

Arg Arg Ala
            115

METHOD OF TREATING LOWER BACK PAIN

CROSS-REFERENCE TO RELATED APPLICATIONS

This application claims the benefit under 35 U.S.C § 119(e) of U.S. provisional application No. 62/427,365, filed Nov. 29, 2016, which is herein specifically incorporated by reference in its entirety.

FIELD OF THE INVENTION

The present invention relates to the treatment, or prevention of low back pain (LBP) in patients who have a history of inadequate pain relief, or intolerance to standard analgesic therapy. More specifically, the invention relates to the administration of NGF antagonists, in particular a nerve growth factor (NGF) antibody, to reduce chronic low back pain in a patient in need thereof.

BACKGROUND

Many patients with acute and chronic pain do not receive adequate pain relief despite the wide variety of analgesic medications that are currently available, either because the medications are not effective in all patients, or because their use is limited by toxicity or intolerability. The limitations of currently available analgesic therapies include adverse central nervous system effects, nausea and vomiting, constipation, gastrointestinal bleeding and ulceration, cardiovascular events, renal toxicity, and potential for abuse. Inadequate pain relief has a profound impact on the quality of life for millions of people worldwide with an associated substantial cost to society, including healthcare cost and loss of productivity.

Neurotrophins are a family of peptide growth factors that play a role in the development, differentiation, survival and death of neuronal and non-neuronal cells (Chao, M. et. al., (2006), ClinSci (Lond); 110:167). Nerve growth factor (NGF) was the first neurotrophin to be identified, and its role in the development and survival of both peripheral and central neurons during the development of the nervous system is well characterized (Smeyne, R. J., et. al., (1994), Nature 368:166-169; Crowley, C. et. al., (1994), 76:1001-1011). In the adult, NGF is not required as a survival factor but acts as a pain mediator that sensitizes neurons (Pezet, S. et. al., (2006), Ann Rev Neurosci 29:507-518). Nerve growth factor activity is mediated through 2 different membrane-bound receptors, the high-affinity tyrosine kinase type 1 (TrkA) and the low-affinity p75 neurotrophin receptors.

Administration of NGF has been shown to provoke pain in both rodents (Lewin, G. R., et. al., (1994), Eur. J. Neurosci 6:1903-1912) and humans (McArthur, J. C., et. al., (2000), Neurology 54:1080-1088), while NGF antagonists have been shown to prevent hyperalgesia and allodynia in animal models of neuropathic and chronic inflammatory pain (Ramer, M. S. et. al., Eur J Neurosci 11:837-846). Humans with mutations in TrkA (hereditary sensory and autonomic neuropathy IV) or NGF (hereditary sensory and autonomic neuropathy V) have been identified with a loss of deep pain perception (Indo, Y. et. al., (1996), Nature Genetics, 13:485-488), Einarsdottir, E., et. al., (2004), Human Molecular Genetics 13:799-805). In addition, NGF is known to be elevated in the synovial fluid of patients with rheumatoid arthritis and other types of arthritis (Aloe, L. et. al., (1992), Arthritis Rheum 35:351-355; Halliday, D. A., (1998), Neurochem Res. 23:919-922), and to be up-regulated in injured and inflamed tissues in conditions such as cystitis, prostatitis, and chronic headache (Lowe, E. M., et. al., (1997), Br. J. Urol. 79:572-577; Miller, L. J., et. al., (2002), Urology 59:603-608; Sarchielli, P. et. al., (2001), Neurology 57:132-134).

There is an unmet need for agents that alleviate pain in individuals who have a history of inadequate pain relief, or who are intolerant to standard analgesic therapy. Fasinumab is a fully-human high-affinity monoclonal antibody directed against NGF. By selectively blocking NGF, fasinumab has the potential to be effective in modulating NGF-associated pain without some of the adverse side effects of other analgesic medications, such as opioids and non-steroidal anti-inflammatory drugs (NSAIDs).

BRIEF SUMMARY OF THE INVENTION

A method of averting opioid addiction in a patient is disclosed. The method can be applied to a patient suffering from moderate to severe low back pain (LBP). The method comprises: diagnosing the patient as suffering from low back; administering to the patient a pharmaceutical composition comprising a therapeutically effective amount of an antibody that binds specifically to nerve growth factor (NGF) or an antigen binding fragment thereof; and avoiding administration of an opioid to the patient, and thereby relieving pain, and averting opioid addiction in a patient.

In an aspect of the invention, the antibody or antigen-binding fragment comprises three heavy chain complementarity determining region (HCDR) sequences (HCDR1, HCDR2, HCDR3) comprising SEQ ID NOs: 4, 6 and 8, respectively, and three light chain complementarity determining (LCDR) sequences (LCDR1, LCDR2, LCDR3) comprising SEQ ID NOs: 12, 14 and 16, respectively.

In another aspect of the invention, the antibody or antigen-binding fragment comprises a heavy chain variable region (HCVR)/light chain variable region (LCVR) amino acid sequence pair of SEQ ID NOs: 2/10.

In yet another aspect of the invention, the patient is diagnosed with chronic, non-radicular back pain.

According to certain aspects of the present invention, methods are provided for treating a patient suffering from moderate to severe low back pain (LBP). In one embodiment, the low back pain is inadequately controlled by standard analgesic therapy. Certain embodiments of the invention pertain to methods for treating, ameliorating or preventing chronic moderate-to-severe low back pain in a patient who exhibits a history of inadequate pain relief, or who is resistant, inadequately responsive, or intolerant to standard analgesic therapy. The methods of the present invention comprise administering to a patient in need thereof a pharmaceutical composition comprising a therapeutically effective amount of a nerve growth factor (NGF) antagonist. According to certain embodiments of the present invention, the NGF antagonist is an antibody or antigen-binding fragment thereof that specifically binds NGF. An exemplary anti-NGF antibody that can be used in the context of the methods of the present invention are described elsewhere herein, including working Example 2. In one embodiment, the NGF antagonist is an anti-NGF antibody referred to herein as "REGN475", or "fasinumab".

In one embodiment, the low back pain to be treated by the NGF antibody of the invention is chronic, non-radicular low back pain.

In certain embodiments, the patient to be treated by the NGF antibody of the invention exhibits a history of inadequate pain relief, or an intolerance to standard analgesic therapy, or may be a patient who is unwilling to take or be treated with standard analgesic therapy, or who does not have access to standard analgesic therapy. In some embodiments, it may be inadvisable for the patient to take standard analgesic therapy due to safety and health risks to the patient and/or the standard analgesic therapy may result in suboptimal efficacy. In certain embodiments, the standard analgesic therapy is inadvisable for administration to the patient due to a condition selected from the group consisting of medical contraindications, hypersensitivity to standard analgesic therapy, or excipients, use of a concomitant medication prohibited with standard analgesic therapy, increased risk of kidney damage, increased risk of liver damage, increased risk of gastrointestinal bleeding, increased risk of an allergic reaction and increased risk of developing drug dependence.

Examples of such analgesic therapy may be selected from the group consisting of paracetamol/acetaminophen, a non-steroidal anti-inflammatory (NSAID), and an opioid. The opioid may be selected from the group consisting of hydrocodone, oxycodone, percocet, morphine, meperidine, hydromorphone, fentanyl, and methadone.

In one embodiment, the NGF antagonist to be used in the methods of the invention is an antibody, or an antigen-binding fragment thereof that binds specifically to NGF and is administered to the patient at a dose of about 6 mg at a frequency of about every 4 weeks. In one embodiment, the NGF antagonist to be used in the methods of the invention is an antibody, or an antigen-binding fragment thereof that binds specifically to NGF and is administered to the patient at a dose of about 6 mg at a frequency of about every 4 weeks, or every 8 weeks, or every 12 weeks. In one embodiment, the NGF antibody or antigen-binding fragment thereof that binds specifically to NGF is administered to the patient at a dose of about 9 mg at a frequency of about every 8 weeks. In one embodiment, the NGF antibody or antigen-binding fragment thereof that binds specifically to NGF is administered to the patient at a dose of about 9 mg at a frequency of about every 4 weeks, every 8 weeks, or every 12 weeks.

In certain embodiments, the NGF antibody is administered either subcutaneously or intravenously.

In certain embodiments, the NGF antibody or antigen-binding fragment thereof is selected from the group consisting of tanezumab, fulranumab and fasinumab.

In one embodiment, the NGF antibody to be used in the methods of the invention is fasinumab, which comprises a heavy chain variable region (HCVR) having the amino acid sequence of SEQ ID NO: 2 and a light chain variable region (LCVR) having the amino acid sequence of SEQ ID NO: 10.

In one embodiment, the antibody or antigen-binding fragment thereof that binds specifically to NGF and is to be used in the methods of the invention comprises complementarity determining regions (CDRs) in a heavy chain variable region (HCVR)/light chain variable region (LCVR) sequence pair of SEQ ID NOs: 2/10.

In one embodiment, the antibody or antigen-binding fragment that binds NGF and is to be used in the methods of the invention comprises three heavy chain complementarity determining region (HCDR) sequences (HCDR1, HCDR2, HCDR3) comprising SEQ ID NOs: 4, 6, and 8, respectively, and three light chain complementarity determining (LCDR) sequences (LCDR1, LCDR2, LCDR3) comprising SEQ ID NOs: 12, 14 and 16, respectively.

In one embodiment, the antibody or antigen-binding fragment that binds NGF and is to be used in the methods of the invention comprises an HCVR having the amino acid sequence of SEQ ID NO:2 and an LCVR having the amino acid sequence of SEQ ID NO: 10.

In one embodiment, the patient, following administration of the pharmaceutical composition comprising fasinumab, exhibits an improvement in one or more pain-associated parameters selected from the group consisting of: (a) a change from baseline at week 16 in the average daily Low Back Pain intensity (LBPI) Numerical Rating Scale (NRS) score; (b) a change from baseline at week 16 in the Roland Morris Disability Questionnaire (RMDQ) total score; (c) a change from baseline at week 16 in the Patient Global Assessment (PGA) of Low Back Pain (LBP) score; and (d) a change from baseline at week 2, 4, 8 and 12 in the average daily LBPI NRS score.

In a related embodiment, the patient being treated with the pharmaceutical composition containing fasinumab may show an improvement in other pain associated parameters including e) a change from baseline at week 16 in the percentage of patients who are responders as defined by a 30% reduction and a 50% reduction in one or more of the following: i) average daily LBPI NRS score; ii) RMDQ total score; and iii) PGA of LBP score.

In another related embodiment, the patient being treated with the pharmaceutical composition containing fasinumab may show an improvement in additional pain associated parameters including f) a change from baseline at week 16 in the Medical Outcomes Study (MOP) sleep subscale score; g) a change from baseline at week 16 in the short form health survey (SF-36) subscale scores; h) a change from baseline at week 16 in the EQ-5D-5L; and i) change from baseline at week 16 in the percentage of patients who use rescue medication for LBP.

In one embodiment, the patient being treated with the pharmaceutical composition containing fasinumab exhibits an improvement in at least one pain associated parameter without experiencing any significant adverse event attributed to treatment with fasinumab.

In another aspect, the invention provides a method for improving one or more pain-associated parameter(s) in a patient suffering from moderate to severe low back pain (LBP), wherein the patient is selected on the basis of exhibiting a history of inadequate pain relief, or intolerance to standard analgesic therapy, or when the standard analgesic therapy is inadvisable for the patient, the method comprising sequentially administering to the patient a single initial dose of a pharmaceutical composition comprising an NGF antagonist that specifically binds NGF, followed by one or more secondary doses of the pharmaceutical composition comprising the NGF antagonist. In one embodiment, the NGF antagonist is an anti-NGF antibody comprising the three HCDRs and the three LCDRs contained within a HCVR/LCVR amino acid sequence pair of SEQ ID NOs: 2/10.

In one embodiment, the low back pain is chronic, non-radicular back pain.

In one embodiment, the standard analgesic therapy is selected from the group consisting of paracetamol/acetaminophen, a non-steroidal anti-inflammatory (NSAID), and an opioid.

In one embodiment, the opioid is selected from the group consisting of hydrocodone, oxycodone, percocet, morphine, meperidine, hydromorphone, fentanyl, and methadone.

In one embodiment, the NGF antagonist is an antibody, or an antigen-binding fragment thereof that binds specifically to NGF. The antibody or antigen-binding fragment thereof may be selected from the group consisting of tanezumab, fulranumab and fasinumab.

In one embodiment, the antibody is fasinumab.

In one embodiment, the antibody or antigen-binding fragment comprises complementarity determining regions (CDRs) in a heavy chain variable region (HCVR)/light chain variable region (LCVR) sequence pair of SEQ ID NOs: 2/10.

In one embodiment, the antibody or antigen-binding fragment that binds NGF comprises three heavy chain complementarity determining region (HCDR) sequences (HCDR1, HCDR2, HCDR3) comprising SEQ ID NOs: 4, 6 and 8, respectively, and three light chain complementarity determining (LCDR) sequences (LCDR1, LCDR2, LCDR3) comprising SEQ ID NOs: 12, 14 and 16, respectively.

In one embodiment, the antibody or antigen-binding fragment that binds NGF comprises an HCVR having the amino acid sequence of SEQ ID NO:2 and an LCVR having the amino acid sequence of SEQ ID NO: 10.

In one embodiment, the initial dose comprises a first amount of the NGF antagonist and the one or more secondary doses each comprise a second amount of the NGF antagonist.

In one embodiment, the initial dose of the pharmaceutical composition is a dose that is equivalent to two times the secondary dose administered to the patient.

In one embodiment, the initial dose and the one or more secondary doses of the pharmaceutical composition comprising the NGF antagonist each comprise about 6.0 mg to about 9.0 mg of the NGF antagonist, wherein the NGF antagonist is an antibody that binds specifically to NGF and comprises an HCVR having the amino acid sequence of SEQ ID NO:2 and an LCVR having the amino acid sequence of SEQ ID NO: 10.

In one embodiment, the initial dose and the one or more secondary doses are administered either subcutaneously or intravenously.

In one embodiment, the one or more secondary doses of the NGF antagonist are administered every four weeks, every eight weeks, or every 12 weeks after the initial dose.

In one embodiment, the one or more secondary doses of the NGF antagonist are administered every four weeks, or every eight weeks after the initial dose.

In one embodiment, the one or more pain-associated parameters are selected from the group consisting of: (a) a change from baseline at week 16 in the average daily Low Back Pain Intensity (LBPI) Numerical Rating Scale (NRS) score; (b) a change from baseline at week 16 in the Roland Morris Disability Questionnaire (RMDQ) total score; (c) a change from baseline at week 16 in the Patient Global Assessment (PGA) of Low Back Pain (LBP) score; and (d) a change from baseline at week 2, 4, 8 and 12 in the average daily LBPI NRS score; e) a change from baseline at week 16 in the percentage of patients who are responders as defined by a 30% reduction and a 50% reduction for (i) average daily LBPI NRS score; (ii) RMDQ total score; and (iii) PGA of LBP score; f) a change from baseline at week 16 in the Medical Outcomes Study (MOP) sleep subscale score; g) a change from baseline at week 16 in the short form health survey (SF-36) subscale scores; h) a change from baseline at week 16 in the EQ-5D-5L; and i) change from baseline at week 16 in the percentage of patients who use rescue medication for LBP.

Other embodiments of the present invention will become apparent from a review of the ensuing detailed description.

BRIEF DESCRIPTION OF THE FIGURES

FIGS. 1A, 1B, 1C and 1D: Provides a summary of the schedule of events during the screening period through week 16 of the study described in Example 2 herein.

FIGS. 2A and 2B: Provides a summary of the schedule of events during the follow-up period from week 20 through week 36 of the study described in Example 2 herein.

FIG. 3 is a summary of the schedule of events for follow-up for patients who undergo total joint replacement surgery in the study described in Example 2 herein.

DETAILED DESCRIPTION

Figure 4:
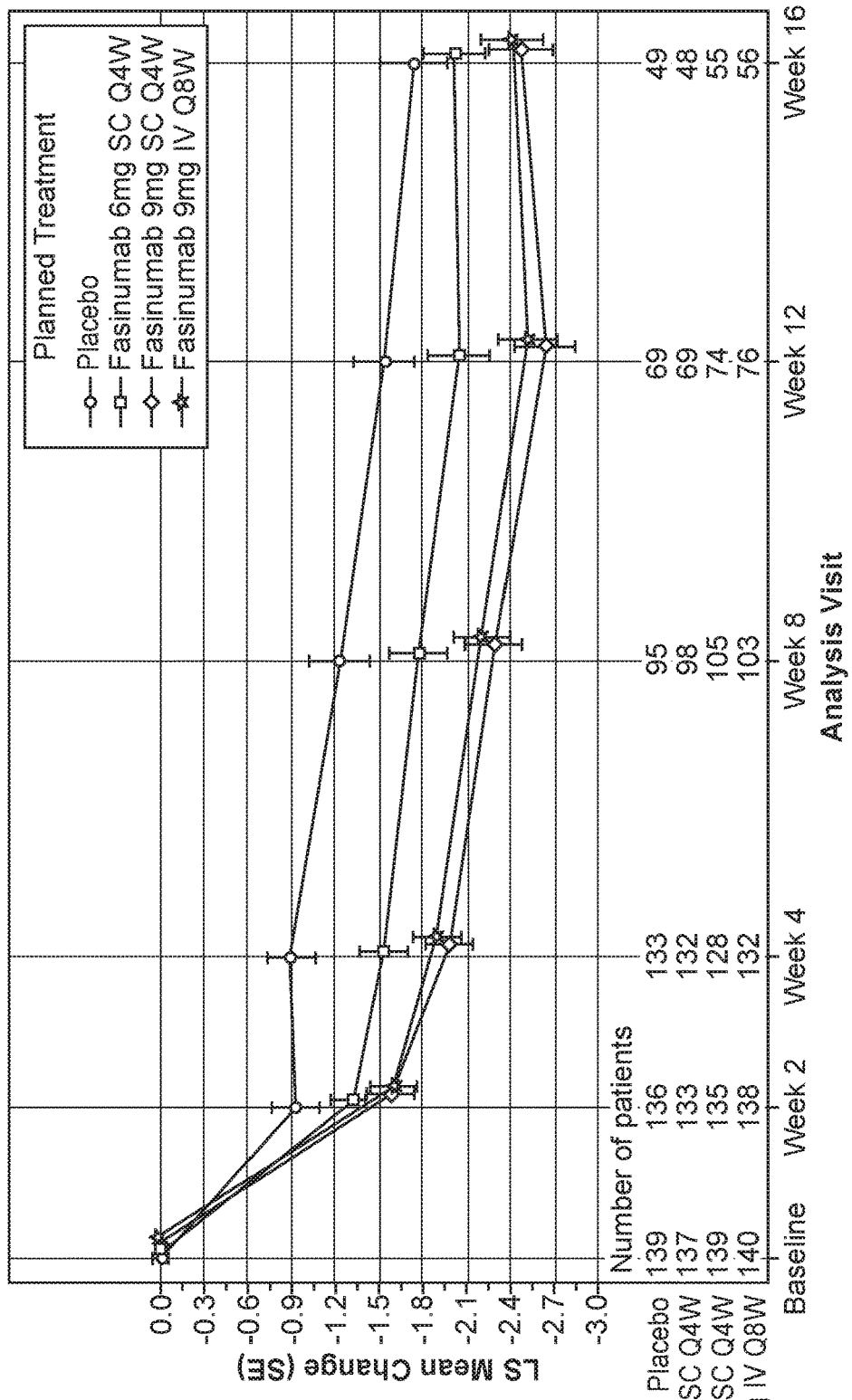
FIG. 4 shows results of the Phase 2/3 study in patients suffering from chronic low back pain: the Change from Baseline in the Low Back Pain Intensity (LBPI) NRS Score (score range: 0 to 10) by Visit: Least Squares Mean (+/−SE) (MITT).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All patents, applications and non-patent publications mentioned herein are incorporated herein by reference in their entireties.

Methods of Treating Chronic Low Back Pain in Selected Patient Populations

The present invention includes methods and compositions for treating patients with moderate to severe chronic non-radicular low back pain who have a history of intolerance to, or inadequate pain relief from standard therapies, including paracetamol/acetaminophen, oral NSAIDS, and opioid therapy. This subset of patients with chronic LBP represents a patient population with an unmet medical need who may benefit from treatment with an NGF antagonist such as fasinumab, which may prove to be efficacious and may provide a better safety profile than other standard therapies.

As described herein, "low back pain", sometimes also referred to herein as "lower back pain", is a common disorder involving the muscles and bones of the back and is characterized as pain, muscle tension, or stiffness localized below the costal margin and above the inferior gluteal folds. Low back pain may be classified by duration as "acute" (pain lasting less than 6 weeks), "sub-chronic" (6 to 12 weeks), or "chronic" (more than 12 weeks). "Chronic" low back pain may originate from an injury, disease or stresses on different anatomic structures of the body, including bones, muscles, ligaments, joints, nerves or the spinal cord. The type of pain may vary greatly and may be felt as bone pain, nerve pain or muscle pain. The sensation of pain may also vary. For instance, pain may be achey, burning, stabbing or tingling, sharp or dull, and well-defined or vague. The intensity may range from mild to severe.

According to certain embodiments of the invention, the patient may be selected for treatment with fasinumab based on presenting with a clinical diagnosis of chronic moderate to severe LBP (non-radiculopathic) for greater than or equal to three months. In certain embodiments, the primary pain suffered by the patient is located between the $12^{th}$ thoracic vertebra and the lower gluteal fold. The patient at both screening and randomization visit should exhibit a LBPI NRS score of greater than or equal to 4 over the previous 24 hours. At the screening visit the PGA of LBP must be fair, poor or very poor.

According to certain embodiments, the patient has a history of regular analgesic medications such as NSAIDS, COX-2 inhibitors, opioids, acetaminophen, or a combination thereof.

According to certain embodiments, the patient has a history of inadequate pain relief or intolerance to analgesics used for chronic LBP as defined by: intolerance or inadequate pain relief from acetaminophen, and intolerance or inadequate pain relief from at least one oral NSAID, and intolerance to, or inadequate pain relief from at least one opioid, unwillingness to take opioid therapy or lack access to opioid therapy.

Low back pain may be classified based on the signs and symptoms. Low back pain accompanied by spinal nerve root damage is usually associated with neurologic signs or symptoms and is described as radiculopathy. There is usually pathologic evidence of spinal nerve root compression by disk or arthritic spur, but other intraspinal pathologies may be present and are often apparent on an MRI scan of the lumbosacral spine. Thus, pain that radiates down the leg below the knee, is located on one side (in the case of disc herniation), or is on both sides (in spinal stenosis), and changes in severity in response to certain positions or maneuvers is "radicular", making up 7% of cases (Manusov E G, (2012), Prim. Care 39 (3): 471-9).

Diffuse pain that does not change in response to particular movements, and is localized to the lower back without radiating beyond the buttocks is classified as "nonspecific", or "non-radicular", the most common classification (Manusov E G, (2012), Prim. Care 39 (3): 471-9). "Nonspecific" or "non-radicular" low back pain is not associated with neurologic symptoms or signs. In general, the pain is localized to the spine or paraspinal regions (or both) and does not radiate into the leg. In general, nonspecific low back pain is not associated with spinal nerve root compression. Nonspecific low back pain might or might not be associated with significant pathology on magnetic resonance imaging (MRI) and is often a result of simple soft tissue disorders such as strain, but it can also be caused by serious medical disorders arising in the bony spine, parameningeal, or retroperitoneal regions.

The present invention includes methods, which comprise administering to a subject in need thereof a therapeutic composition comprising an NGF antagonist. As used herein, the expression "a subject in need thereof" means a human that exhibits low back pain. In certain embodiments, "a subject in need thereof" refers to a patient suffering from chronic, non-radicular low back pain. In certain embodiments, "a subject in need thereof" refers to a patient suffering from chronic low back pain, who has a history of inadequate pain relief, or intolerance to standard analgesic therapy. In certain embodiments, the methods of the present invention may be used to treat patients that show elevated levels of one or more pain-associated parameters (described elsewhere herein).

In the context of the present invention, "a subject in need thereof" may also include, e.g., subjects who, prior to treatment, exhibit (or have exhibited) one or more pain-associated parameters, which are improved following treatment with an anti-NGF antibody of the present invention.

In one embodiment, the patient, following administration of a pharmaceutical composition comprising fasinumab, exhibits an improvement in one or more pain-associated parameters selected from the group consisting of: (a) a change from baseline at week 16 in the average daily Low Back Pain intensity (LBPI) Numerical Rating Scale (NRS) score; (b) a change from baseline at week 16 in the Roland Morris Disability Questionnaire (RMDQ) total score; (c) a change from baseline at week 16 in the Patient Global Assessment (PGA) of Low Back Pain (LBP) score; (d) a change from baseline at week 2, 4, 8 and 12 in the average daily LBPI NRS score; e) a change from baseline at week 16 in the percentage of patients who are responders as defined by a 30% reduction and a 50% reduction for (i) average daily LBPI NRS score; (ii) RMDQ total score; and (iii) PGA of LBP score; f) a change from baseline at week 16 in the Medical Outcomes Study (MOP) sleep subscale score; g) a change from baseline at week 16 in the short form health survey (SF-36) subscale scores; h) a change from baseline at week 16 in the EQ-5D-5L; and i) change from baseline at week 16 in the percentage of patients who use rescue medication for LBP.

The severity of the pain is assessed using standard methods known to those skilled in the art. For example, using methods including those described herein, such as the Low Back Pain Intensity (LBPI) Numerical Rating Scale (NRS) score; the Roland Morris Disability Questionnaire (RMDQ) total score; or the Patient Global Assessment (PGA) of Low Back Pain (LBP) score (See Mannion, A F, et al. Nature Clinical Practice Rheumatology (2007) 3: 610-618.

Various instruments have been developed to evaluate pain intensity (how much a person hurts) and pain affect (how much a person suffers). Three methods have traditionally been used to measure pain intensity: visual analogue scales (VASs), verbal rating scales (VRSs), and numerical rating scales (NRSs). ☐ See Von Korff M et al. (2000), Spine 25: 3140-3151; Zanoli G et al. (2000), Spine 25: 3178-3185; Haefeli M and Elfering A (2006), Eur Spine J 15 (Suppl 1): S17-S24; McGuire D B (1999), Instruments for Health-Care Research 528-561 (Eds Frank-Stromborg M and Olsen S) Boston: Jones and Bartlett; Ogon M et al. (1996), Pain 64: 425-428; Hägg O et al. (2003), Eur Spine J 12: 12-20; Jensen M P et al. (1986), Pain 27: 117-126).

The visual analogue scale (VAS) consists of a line, usually 100 mm long, whose ends are labeled as the extremes ('no pain' and 'pain as bad as it could be'); the rest of the line is blank. The patient is asked to put a mark on the line indicating their pain intensity (at the present time, over the past week, or over the past 2 weeks, etc.). The distance between that mark and the origin is measured to obtain the patient's score. Sometimes descriptive terms, such as 'mild', 'moderate' and 'severe', or numbers are provided along the scale for guidance, with "moderate" falling within the midrange of the scale and the scale is then referred to as a graphic rating scale.

Verbal rating scales (VRSs) consist of a list of adjectives that describe different levels of pain intensity. A VRS for pain includes adjectives that reflect the extremes (e.g. 'no pain' to 'pain as bad as it could be'), and sufficient adjectives to capture the gradations in between. VRSs are most frequently five-point or six-point scales. The patient is asked to select in a questionnaire or state verbally the adjective that best describes his or her level of pain intensity. In behavioral rating scales, different pain levels are described by sentences including behavioral parameters.

The numeric rating scale (NRS) involves asking patients to rate their pain intensity by selecting a number on a scale from 0-10 (11-point scale), 0-20 (21-point scale), or 0-100 (101-point scale) by filling in a questionnaire or stating verbally a numerical level. For example, a zero (0) would mean "no pain" and a one hundred (100) would mean "pain as bad as it could be". The patient is asked to write only one number. For example, using the 0-10 NRS, a patient exhibiting "moderate LBP" may enter a number between 4-6 for "moderate pain" and between 7-10 for "severe pain". See the exemplary table below.

| Rating | Pain Level |
| --- | --- |
| 0 | No Pain |
| 1-3 | Mild Pain (nagging, annoying, interfering little with activity of daily living (ADLs) |
| 4-6 | Moderate Pain (interferes significantly with ADLs) |
| 7-10 | Severe Pain (disabling; unable to perform ADLs) |

A patient may also be said to have moderate-to-severe low back pain when the patient is resistant or refractory to treatment by standard analgesics, such as acetaminophen or an NSAID, or any other commonly used therapeutic agent known in the art for treating low back pain.

As noted above, the present invention includes methods to treat chronic low back pain in patients who exhibit a history of inadequate pain relief, or intolerance to standard analgesic therapy, or who are resistant, non-responsive or inadequately responsive to treatment with a standard analgesic. The term "inadequate pain relief" refers to an unacceptable level of pain relief experienced by subjects after treatment with a standard analgesic, who may find that they cannot go about conducting normal daily activities due to the pain level index.

The term "intolerance to standard analgesic therapy" refers to subjects or patients who, for example, are allergic to a standard analgesic, or who exhibit an adverse event after treatment with the standard analgesic. The term "resistant, non-responsive or inadequately responsive to a standard analgesic", as used herein, refers to subjects or patients with LBP who have been treated with for example, an NSAID, and wherein the NSAID does not have a therapeutic effect. In some embodiments, the term refers to reduced patient compliance and/or toxicity and side effects and/or ineffectiveness of the administered analgesic to reduce, ameliorate or decrease the symptoms of LBP. In some embodiments, the term refers to patients suffering from moderate-to-severe LBP who are refractory to treatment by a standard analgesic. In some embodiments, the patients who are "resistant, non-responsive or inadequately responsive to a standard analgesic" may show no improvement in one or more pain-associated parameters. Examples of pain-associated parameters are described elsewhere herein. For example, treatment with a standard analgesic may result in no change in the LBPI NRS score, or in the Roland Morris Disability Questionnaire (RMDQ) total score. In some embodiments, the present invention includes methods to treat moderate-to-severe LBP in patients who have been treated earlier with an analgesic, e.g. for ≥1 month and do not show a change (e.g. a decrease) in one or more pain-associated parameters.

Although any methods and materials similar or equivalent to those described herein can be used in the practice of the present invention, the preferred methods and materials are now described. All publications mentioned herein are incorporated herein by reference to describe in their entirety.

Methods for Improving Pain-Associated Parameters: Therapeutic Efficacy Measurements The present invention includes methods for improving one or more pain-associated parameters in a subject in need thereof, wherein the methods comprise administering a pharmaceutical composition comprising an NGF antagonist, e.g., an anti-NGF antibody of the invention, to the subject.

Examples of "pain-associated parameters" include: (a) the Low Back Pain intensity (LBPI) Numerical Rating Scale (NRS) score; (b) the Roland Morris Disability Questionnaire (RMDQ) total score; (c) the Patient Global Assessment (PGA) of Low Back Pain (LBP) score; (d) the Medical Outcomes Study (MOP) sleep subscale score; (e) the short form health survey (SF-36) subscale scores; (f) the EQ-5D-5L; and (g) the percentage of patients who use rescue medication for LBP.

An "improvement in a pain-associated parameter" means a significant change from baseline in one or more of the following: (a) a change from baseline at week 16 in the average daily Low Back Pain intensity (LBPI) Numerical Rating Scale (NRS) score; (b) a change from baseline at week 16 in the Roland Morris Disability Questionnaire (RMDQ) total score; (c) a change from baseline at week 16 in the Patient Global Assessment (PGA) of Low Back Pain (LBP) score; or (d) a change from baseline at week 2, 4, 8 and 12 in the average daily LBPI NRS score. In addition, an "improvement in a pain-associated parameter" means a significant change from baseline in one or more of the following: (e) a change from baseline at week 16 in the percentage of patients who are responders as defined by a 30% reduction and a 50% reduction for (i) average daily LBPI NRS score; (ii) RMDQ total score; and (iii) PGA of LBP score; or (f) a change from baseline at week 16 in the Medical Outcomes Study (MOP) sleep subscale score; or (g) a change from baseline at week 16 in the short form health survey (SF-36) subscale scores; or (h) a change from baseline at week 16 in the EQ-5D-5L; or i) a change from baseline at week 16 in the percentage of patients who use rescue medication for LBP.

As used herein, the term "baseline," with regard to a pain-associated parameter, means the numerical value of the pain-associated parameter for a subject prior to or at the time of administration of a pharmaceutical composition of the present invention.

To determine whether a pain-associated parameter has "improved," the parameter is quantified at baseline and at one or more time points after administration of the pharmaceutical composition of the present invention. For example, a pain-associated parameter may be measured at various time points after administration of fasinumab, e.g., at day 1, day 2, day 3, day 4, day 5, day 6, day 7, day 8, day 9, day 12, day 18, day 22, day 36, day 50, day 57, day 64, day 78, day 85, day 92, day 106, day 113, day 120; or at the end of week 1, week 2, week 3, week 4, week 5, week 6, week 7, week 8, week 9, week 10, week 11, week 12, week 13, week 14, week 15, week 16, or longer, after the initial treatment with a pharmaceutical composition of the present invention. The difference between the value of the parameter at a particular time point following initiation of treatment and the value of the parameter at baseline is used to establish whether there has been an "improvement" (e.g., a decrease) in the pain associated parameter.

The Low Back Pain Intensity-Numeric Rating Scale: The low back pain intensity (LB PI) numeric rating scale (NRS) involves asking patients to rate their pain intensity by selecting a number on a scale from 0-10 (11-point scale), 0-20 (21-point scale), or 0-100 (101-point scale) by filling in a questionnaire or stating verbally a numerical level. For example "Please indicate on the line below the number between 0 and 100 that best describes your pain. A zero (0) would mean 'no pain' and a one hundred (100) would mean 'pain as bad as it could be'. Please write only one number." An empty box or line is provided for the corresponding number to be entered. A slight variation of the NRS is the box scale, where each number (e.g. 0-10) is written in a box and patients are asked: "If a zero (0) means 'no pain' and a ten (10) means 'pain as bad as it could be', on this scale of 0-10, what is your level of pain? Put an "X" through that number." According to certain embodiments of the present invention, administration of an NGF antagonist to a patient results in a decrease in LBPI NRS score. For example, the present invention includes therapeutic methods which result in a decrease from baseline in LBPI NRS score of at least about 10%, 20%, 30%, 40%, 50%, or more at week 2,4,8,12 and 16, or later following administration of the NGF antagonist (e.g., following administration of about 6 mg, or 9 mg of an anti-NGF antibody or antigen-binding fragment thereof).

The Roland Morris Disability Questionnaire: The RMDQ is a self-administered, widely used health status measure for LBP (Roland M O, Morris R W, Spine 1983; 8: 141-144). It measures pain and function, using 24 items describing limitations to everyday life that can be caused by LBP. The score of the RMDQ is the total number of items checked—i.e. from a minimum of 0 to a maximum of 24. The Roland-Morris disability questionnaire is constructed by choosing statements from the sickness impact profile (SIP), which is a 136-item health status measure covering a range of aspects of daily living about physical and mental function. The scale consists of 24 yes/no items related specifically to physical functions to specifically assess the disability from LBP. The physical functions considered include walking, bending over, sitting, lying down, dressing, sleeping, self-care and daily activities. Patients are asked whether the statements apply to them that day (i.e. the last 24 h). In the scale, one point is given for each item. The RDQ score can be obtained by adding up the number of items checked. The final score ranges from 0 (no disability) to 24 (severe disability). According to certain embodiments of the present invention, administration of an NGF antagonist to a patient results in a decrease in RMDQ score. For example, the present invention includes therapeutic methods which result in a decrease from baseline in RMDQ score of at least about 2 to 5 points for a moderate improvement and greater than 5 points to be considered a large, or substantial improvement at week 2, 4, 8, 12 and 16, or later following administration of the NGF antagonist (e.g., following administration of about 6 mg, or 9 mg of an anti-NGF antibody or antigen-binding fragment thereof).

Patient Global Assessment of Low Back Pain: The PGA of LBP is a patient-rated assessment of their current disease state on a 5-point Likert scale (1=very well; 2=well; 3=fair; 4=poor; and 5=very poor). According to certain embodiments of the present invention, administration of an NGF antagonist to a patient results in a decrease in PGA of LBP score. For example, the present invention includes therapeutic methods which result in a decrease from baseline in PGA of LBP score of at least about 1 point, or 2 points, or 3 points or more at week 2, 4, 8, 12 and 16, or later following administration of the NGF antagonist (e.g., following administration of about 6 mg, or 9 mg of an anti-NGF antibody or antigen-binding fragment thereof).

Short Form (36) Health Survey: The SF-36 is a self-administered survey of general health. It measures 8 domains of health: physical functioning, role limitations due to physical health, bodily pain, general health perceptions, vitality, social functioning, role limitations due to emotional problems, and mental health. It yields scale scores for each of these 8 health domains, and 2 summary measures of physical and mental health: the physical component summary and the mental component summary. Each scale is directly transformed into a 0-100 scale on the assumption that each question carries equal weight. The lower the score the more disability. The higher the score the less disability i.e., a score of zero is equivalent to maximum disability and a score of 100 is equivalent to no disability. According to certain embodiments of the present invention, administration of an NGF antagonist to a patient results in an increase in SF-36 score. For example, the present invention includes therapeutic methods which result in an increase from baseline in SF-36 score of at least about 10%, 20%, 30%, 40%, 50%, or more at week 2, 4, 8, 12 and 16, or later following administration of the NGF antagonist (e.g., following administration of about 6 mg, or 9 mg of an anti-NGF antibody or antigen-binding fragment thereof).

Medical Outcomes Study Sleep Survey: The MOS Sleep Survey is a self-administered 12-question survey of sleep habits (Hays R D, Stewart A L (1992). Sleep measures. In A. L. Stewart & J. E. Ware (eds.), Measuring functioning and well-being: The Medical Outcomes Study approach (pp 235-259), Durham, N.C.: Duke University Press). According to certain embodiments of the present invention, administration of an NGF antagonist to a patient results in an improvement in the MOS Sleep Survey from baseline. For example, the present invention includes therapeutic methods which result in a change from baseline in the MOS Sleep Survey at week 2, 4, 8, 12 and 16, or later following administration of the NGF antagonist (e.g., following administration of about 6 mg, or 9 mg of an anti-NGF antibody or antigen-binding fragment thereof).

EQ-5D-5L: The EQ-5D-5L is a standardized measure of health status developed by the EuroQol Group to provide a simple, generic measure of health for clinical and economic appraisal. The EQ-5D-5L, as a measure of health-related quality of life, defines health in terms of 5 dimensions: mobility, self-care, usual activities, pain/discomfort, anxiety/depression. Each dimension has 3 ordinal levels of severity: "no problem" (1), "some problems" (2), "severe problems" (3). Overall health state is defined as a 5-digit number. Health states defined by the 5-dimensional classification can be converted into corresponding index scores that quantify health status, where −0.594 represents "severe problems" and 1 represents "no problem." According to certain embodiments of the present invention, administration of an NGF antagonist to a patient results in an improvement in the EQ-5D-5L from baseline. For example, the present invention includes therapeutic methods which result in a change from baseline in the EQ-5D-5L at week 2, 4, 8, 12 and 16, or later following administration of the NGF antagonist (e.g., following administration of about 6 mg, or 9 mg of an anti-NGF antibody or antigen-binding fragment thereof).

NGF Antagonists

As disclosed in detail above, the present invention includes methods, which comprise administering to a subject in need thereof a therapeutic composition comprising an NGF antagonist. As used herein, an "NGF antagonist" is any agent, which binds to or interacts with NGF and inhibits the normal biological function of NGF when NGF is expressed on a cell in vitro or in vivo. Non-limiting examples of categories of NGF antagonists include small molecule NGF antagonists, anti-NGF aptamers, peptide-based NGF antagonists (e.g., "peptibody" molecules), and antibodies or antigen-binding fragments of antibodies that specifically bind human NGF.

The terms "NGF," "hNGF," and the like, as used herein, are intended to refer to nerve growth factor, and in particular, to human nerve growth factor, the amino acid sequence of which is shown as SEQ ID NO: 18 and which is encoded by the nucleic acid sequence shown as SEQ ID NO: 17. Unless specifically designated as being from a non-human species, the term "NGF", as used herein, shall be understood to mean human NGF.

The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The VH and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-NGF antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" NGF, as used in the context of the present invention, includes antibodies that bind NGF or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, less than about 0.5 nM, less than 0.1 nM, less than 1.0 pM, or less than 0.5 pM, as measured in a surface plasmon resonance assay. An isolated antibody that specifically binds human NGF may, however, have cross-reactivity to other antigens, such as NGF molecules from other (non-human) species.

The anti-NGF antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-NGF antibodies comprising variants of any of the HCVR, LCVR, and/or CDR amino acid sequences disclosed herein having one or more conservative substitutions. For example, the present invention includes the use of anti-NGF antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance," as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$," as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used in the context of the present invention to make human antibodies that specifically bind to human NGF.

Using VELOCIMMUNE™ technology (see, for example, U.S. Pat. No. 6,596,541, Regeneron Pharmaceuticals) or any other known method for generating monoclonal antibodies, high affinity chimeric antibodies to NGF are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind NGF which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence consisting of SEQ ID NO: 2. The antibody or antigen-binding fragment may comprise the three light chain CDRs (LCVR1, LCVR2, LCVR3) contained within a light chain variable region (LCVR) having an amino acid sequence consisting of SEQ ID NO: 10. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest,"

National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) of SEQ ID NOs: 2/10.

In certain embodiments of the present invention, the antibody or antigen-binding fragment thereof comprises six CDRs (HCDR1/HCDR2/HCDR3/LCDR1/LCDR2/LCDR3) having the amino acid sequences consisting of SEQ ID NOs: 4/6/8/12/14/16.

In certain embodiments of the present invention, the antibody or antigen-binding fragment thereof comprises HCVR/LCVR amino acid sequence pairs consisting of SEQ ID NOs: 2/10.

Pharmaceutical Compositions

The present invention includes methods, which comprise administering an NGF antagonist to a patient, wherein the NGF antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-NGF antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351). Specific exemplary doses of anti-IL4R antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-NGF antibody that can be used in the context of the present invention are disclosed, e.g., in US Patent Application Publication No. 2012/0097565.

Dosage

The amount of NGF antagonist (e.g., anti-NGF antibody) administered to a subject according to the methods of the present invention is, generally, a therapeutically effective amount. As used herein, the phrase "therapeutically effective amount" means an amount of NGF antagonist that results in one or more of: (a) an improvement in one or more pain-associated parameters (as defined elsewhere herein); and/or (b) a detectable improvement in one or more symptoms or indicia of pain. A "therapeutically effective amount" also includes an amount of NGF antagonist that inhibits, prevents, lessens, or delays the progression of pain in a subject.

In the case of an anti-NGF antibody, a therapeutically effective amount can be from about 0.05 mg to about 600 mg, e.g., about 0.05 mg, about 0.1 mg, about 1.0 mg, about 1.5 mg, about 2.0 mg, about 3.0 mg, about 6.0 mg, about 9.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-NGF antibody. In certain embodiments, 6 mg, or 9 mg of an anti-NGF antibody is administered to a subject.

The amount of NGF antagonist contained within the individual doses may be expressed in terms of milligrams of antibody per kilogram of patient body weight (i.e., mg/kg). For example, the NGF antagonist may be administered to a patient at a dose of about 0.0001 to about 10 mg/kg of patient body weight.

Combination Therapies

The methods of the present invention, according to certain embodiments, comprise administering to the subject one or more additional therapeutic agents in combination with the NGF antagonist. As used herein, the expression "in combination with" means that the additional therapeutic agents are administered before, after, or concurrent with the pharmaceutical composition comprising the NGF antagonist. The term "in combination with" also includes sequential or concomitant administration of NGF antagonist and a second therapeutic agent.

For example, when administered "before" the pharmaceutical composition comprising the NGF antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the NGF antagonist. When administered "after" the pharmaceutical composition comprising the NGF antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the NGF antagonist. Administration "concurrent" or with the pharmaceutical composition comprising the NGF antagonist means that the additional therapeutic agent is administered to the subject in a separate dosage form within less than 5 minutes (before, after, or at the same time) of administration of the pharmaceutical composition comprising the NGF antagonist, or administered to the subject as a single combined dosage formulation comprising both the additional therapeutic agent and the NGF antagonist.

The additional therapeutic agent may be, e.g., another NGF antagonist (e.g. see the NGF antibodies described in U.S. Pat. No. 7,449,616 (tanezumab); U.S. Pat. Nos. 7,569,364; 7,655,232; 8,088,384; WO2011049758 (fulranumab)), an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an opioid, acetaminophen, a local anesthetic, an NMDA modulator, a cannabinoid receptor agonist, a P2X family modulator, a VR1 antagonist, a substance P antagonist, a Nav1.7 antagonist, a cytokine or cytokine receptor antagonist, an antiepileptic drug, a steroid, other inflammatory inhibitors such as inhibitors of caspase-1, p38, IKK1/2, CTLA-4Ig and a corticosteroid.

Administration Regimens

The present invention includes methods comprising administering to a subject a pharmaceutical composition comprising an NGF antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-NGF antibody, such as fasinumab, once every 4 weeks dosing at an amount of about 3, 6, or 9 mg, can be employed. In certain embodiments involving the administration of a pharmaceutical composition comprising an anti-NGF antibody, such as fasinumab, once every 8 weeks dosing at an amount of about 3, 6, or 9 mg, can be employed. In certain embodiments involving the administration of a pharmaceutical composition comprising an anti-NGF antibody, such as fasinumab, once every 12 weeks dosing at an amount of about 3, 6, or 9 mg, can be employed.

According to certain embodiments of the present invention, multiple doses of an NGF antagonist may be administered to a subject over a defined time course. The methods according to this aspect of the invention comprise sequentially administering to a subject multiple doses of an NGF antagonist. As used herein, "sequentially administering" means that each dose of NGF antagonist is administered to the subject at a different point in time, e.g., on different days separated by a predetermined interval (e.g., hours, days, weeks or months). The present invention includes methods which comprise sequentially administering to the patient a single initial dose of an NGF antagonist, followed by one or more secondary doses of the NGF antagonist, and optionally followed by one or more tertiary doses of the NGF antagonist.

The terms "initial dose," "secondary doses," and "tertiary doses," refer to the temporal sequence of administration of the NGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of NGF antagonist, but generally may differ from one another in terms of frequency of administration. In certain embodiments, however, the amount of NGF antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an NGF antagonist may be administered to a patient with low back pain at a loading dose equivalent to 2 times the maintenance dose. Accordingly, if the maintenance dose is 3 mg, the loading dose will be 6 mg. If the maintenance dose is 6 mg, the loading dose is 12 mg. If the maintenance dose is 9 mg, the loading dose is 18 mg. Accordingly, it is envisioned that a loading dose of about 6 mg, 12 mg, or 18 mg, followed by one, two, or more maintenance doses of about 3 mg, 6 mg, or 9 mg respectively, may be sufficient to achieve a change from baseline in at least one pain parameter as noted herein.

In one exemplary embodiment of the present invention, each secondary and/or tertiary dose is administered 1 to 16 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, or more) weeks after the immediately preceding dose. In one exemplary embodiment of the present invention, each secondary and/or tertiary dose is administered every 4, 8, or 12 weeks after the immediately preceding dose. The phrase "the immediately preceding dose," as used herein, means, in a sequence of multiple administrations, the dose of NGF antagonist, which is administered to a patient prior to the administration of the very next dose in the sequence with no intervening doses.

The methods according to this aspect of the invention may comprise administering to a patient any number of secondary and/or tertiary doses of an NGF antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose, or 4 to 8 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an NGF antagonist and a second therapeutic agent, to a patient to treat chronic low back pain. In some embodiments, the present methods comprise administering one or more doses of an NGF antagonist followed by one or more doses of a second therapeutic agent. For example, one or more doses of about 1 mg to about 20 mg of the NGF antagonist may be administered after which one or more doses of a second therapeutic agent (e.g., acetaminophen, or an opioid or any other therapeutic agent, as described elsewhere herein) may be administered to treat, alleviate, reduce or ameliorate one or more symptoms of chronic low back pain. In some embodiments, the NGF antagonist is administered at one or more doses resulting in an improvement in one or more pain-associated parameters followed by the administration of a second therapeutic agent to prevent recurrence of at least one symptom of low back pain. Alternative embodiments of the invention pertain to concomitant administration of an NGF antagonist and a second therapeutic agent. For example, one or more doses of an NGF antagonist are administered and a second therapeutic agent is administered at a separate dosage at a similar or different frequency relative to the NGF antagonist. In some embodiments, the second therapeutic agent is administered before, after or concurrently with the NGF antagonist.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human NGF

Human anti-NGF antibodies were generated as described in U.S. Pat. No. 7,988,967. The exemplary NGF antagonist used in the following Example is the human anti-NGF antibody designated "REGN475," also known as "fasinumab". Fasinumab has the following amino acid sequence characteristics: a heavy chain variable region (HCVR) comprising SEQ ID NO: 2 and a light chain variable domain (LCVR) comprising SEQ ID NO:10; a heavy chain complementarity determining region 1 (HCDR1) comprising SEQ ID NO:4, a HCDR2 comprising SEQ ID NO:6, a HCDR3 comprising SEQ ID NO:8, a light chain complementarity determining region 1 (LCDR1) comprising SEQ ID NO:12, a LCDR2 comprising SEQ ID NO:14 and a LCDR3 comprising SEQ ID NO:16. See Table 1A. The nucleic acids encoding the HCVR, LCVR, HCDRs and LCDRs of fasinumab are exemplified by the sequence identifiers shown in Table 1B.

TABLE 1A

AMINO ACID SEQ ID NOs:

| Antibody Designation | HC VR | HCDR 1 | HCDR 2 | HCDR 3 | LC VR | LCDR 1 | LCDR 2 | LCDR 3 |
|---|---|---|---|---|---|---|---|---|
| Fasinumab | 2 | 4 | 6 | 8 | 10 | 12 | 14 | 16 |

TABLE 1B

NUCLEIC ACID SEQ ID NOs:

| Antibody Designation | HC VR | HCDR 1 | HCDR 2 | HCDR 3 | LC VR | LCDR 1 | LCDR 2 | LCDR 3 |
|---|---|---|---|---|---|---|---|---|
| Fasinumab | 1 | 3 | 5 | 7 | 9 | 11 | 13 | 15 |

Example 2

A Randomized, Double-Blind, Multi-Dose, Placebo-Controlled Phase 2/3 Study to Evaluate the Efficacy and Safety of Fasinumab in Patients with Moderate to Severe Chronic Low Back Pain (LBP)

Study Objectives

The primary objective of the study was to evaluate the efficacy of fasinumab compared to placebo in reducing LBP, as measured by the change from baseline at week 16 in the average daily Lower Back Pain Intensity (LB PI) Numerical Rating Score (NRS).

The secondary objectives of the study were to evaluate the efficacy of fasinumab compared to placebo in treating LBP as measured by: (a) Change from baseline at week 16 in the RMDQ total score; (b) Change from baseline at week 16 in the PGA of LBP score; (c) Change from baseline at week 2, 4, 8, and 12 in the average daily LBPI NRS score.

The safety objectives of the study were: (a) To assess the safety and tolerability of fasinumab compared with placebo in patients with LBP by evaluating: (i) the percent of patients reporting TEAEs; (ii) the percent of patients experiencing clinically significant changes in vital signs, physical exams, laboratory safety tests, and electrocardiograms (ECGs); (iii) to assess the incidence of anti-fasinumab antibody formation.

Other exploratory objectives of the study included: (a) evaluation of the efficacy of fasinumab compared to placebo, as measured by the percentage of patients who were responders defined by 30% reduction and 50% reduction from baseline to week 16 for: (i) the average daily LBPI NRS score; (ii) the RMDQ total score; (iii) the PGA of LBP score.

Further exploratory objectives of the study included: (a) the evaluation of the efficacy of fasinumab compared to placebo, as measured by the change from baseline at week 16 in the Medical Outcomes Study (MOS) sleep subscale score; (b) the evaluation of the efficacy of fasinumab compared to placebo, as measured by the change from baseline at week 16 in the Short Form (36) Health Survey (SF-36) subscale scores; (c) the evaluation of the efficacy of fasinumab compared to placebo, as measured by the change from baseline at week 16 in the EuroQol 5 Dimensions 5 Levels Questionnaire (EQ-5D-5L); (d) the evaluation of the efficacy of fasinumab compared to placebo, as measured by the percentage of patients who use rescue medication for LBP at week 16; (e) the characterization of the PK profile of fasinumab.

Study Design

This study was a randomized, double-blind, multi-dose, placebo-controlled study designed to evaluate the safety and efficacy of fasinumab in patients with moderate to severe chronic non-radicular LBP who have a history of intolerance or inadequate pain relief from standard analgesics, such as paracetamol/acetaminophen, oral NSAIDs, and opioid therapy.

The study consisted of a screening period of up to 30 days (day −37 to day −8), a 7-day pre-randomization period (day −7 to day −1), a 16-week randomized, double-blind, placebo-controlled treatment period (to day 113), and a 20-week follow-up period. Approximately 563 patients were randomized in a 1:1:1:1 ratio to one of the following 4 treatment groups: (a) Fasinumab 6 mg SC every 4 weeks (Q4W) and placebo 9 mg IV every 8 weeks (Q8W); (b) Fasinumab 9 mg SC Q4W and placebo 9 mg IV Q8W; (c) Fasinumab 9 mg IV Q8W and placebo 9 mg SC Q4W; (d) Placebo 6 mg or 9 mg SC Q4W and placebo 9 mg IV Q8W.

Randomization was stratified by baseline LBPI NRS score (<7, ≥7), duration of chronic back pain (<5 years, ≥5 years), and maximum Kellgren-Lawrence (K-L) score (≤2, >2) at any knee or hip joint at screening.

Screening Period (up to 30 days before the pre-randomization visit): After informed consent was signed, patients were screened for eligibility for enrollment based on study eligibility criteria. During the screening period, patients may continue to take their current treatment regimen for LBP.

Pre-Randomization Period (7 days before the randomization/baseline visit [day 1]): Patients who met the initial eligibility criteria, as assessed during the screening period, were instructed in the use of the electronic diary (EDiary) for recording daily use of rescue medication and LBPI score using the NRS.

Patients were instructed to stop using all prohibited medications at the pre-randomization visit. Patients received paracetamol/acetaminophen to be used as study-provided rescue medication. In the event of inadequate LBP relief, paracetamol/acetaminophen was taken as needed, according to local standard of care, to a maximum total dose of 2600 mg per day, starting at the pre-randomization visit through week 16.

Patients had a mean daily LBPI NRS score ≥4 during the pre-randomization period, in order to be eligible for study participation. Patients were not to use paracetamol/acetaminophen for 48 hours prior to the start of a scheduled study visit or during a study visit, in order to minimize the confounding effects of rescue medication on efficacy measures.

Confirmation that there were no exclusionary findings on lumbar MRI or any hip or knee MRI of joints with a K-L score >3 must have been received before a patient was randomized.

Treatment Period (Day 1 through week 16): The treatment period began at the randomization visit (baseline/day 1) and continued through the week 16 visit. Patients who met study entry criteria were randomized and had baseline assessments at the day 1 visit. For patients randomized to SC administration, a loading dose equivalent to 2 times the maintenance dose was administered on day 1.

Patients randomized to 6 mg or 9 mg fasinumab SC Q4W and placebo IV 9 mg Q8W received 4 SC injections of fasinumab (on day 1 [SC loading dose]) and at weeks 4, 8, and 12), and 2 doses of matching placebo IV (day 1 and week 8).

Patients randomized to 9 mg fasinumab IV Q8W and placebo 9 mg SC Q4W received 2 infusions of fasinumab (day 1 and week 8) and 4 doses of matching placebo to fasinumab SC (day 1 [SC loading dose]) and weeks 4, 8, and 12).

Patients randomized to placebo 6 mg or 9 mg SC Q4W and placebo 9 mg IV Q8W received 4 doses of matching placebo to fasinumab SC (day 1 [SC loading dose] and weeks 4, 8, and 12), and 2 doses of matching placebo IV (day 1 and week 8).

Study drug (fasinumab or placebo) was administered at the study site. Patients were observed in the clinic for approximately 2 hours after IV administration of study drug and for 1 hour after SC dosing for evidence of a hypersensitivity reaction.

Paracetamol/acetaminophen was taken as rescue medication in the event of inadequate LBP relief, as described previously. The use of paracetamol/acetaminophen was prohibited for 48 hours prior to the start of each scheduled study visit in order to minimize the confounding effects of rescue medication on study measures.

Every day, patients reported their LBPI scores using the NRS and their daily use of rescue medication for LBP in the EDiary.

Efficacy and safety assessments were performed as outlined. Potential events of destructive arthropathy were monitored via clinical signs and symptoms of worsening joint pain during the study (eg, using the joint pain questionnaire and imaging). Potential events of sympathetic nervous system dysfunction were monitored throughout the study via the Survey of Autonomic Symptoms.

Follow-up Period (week 20 through week 36 visits): The follow-up period started after the week 16 visit and continued through the week 36 visit.

During the follow-up period, safety and efficacy assessments were performed. Potential events of destructive arthropathy and sympathetic nervous dysfunction were monitored as described previously.

A comprehensive risk management approach was implemented for 2 adverse events of special interest (AESI), destructive arthropathy and sympathetic nervous system dysfunction.

In order to monitor for outcomes for potential cases of destructive arthropathy, if a patient must undergo total joint replacement (TJR) surgery during the study, they were asked to complete an early termination visit prior to the surgery if at all possible and to return for post-surgery follow-up.

Patient Selection

The study enrolled approximately 141 patients in each of 4 treatment groups, for a total of approximately 563 randomized patients at sites in the United States, Canada, and Europe.

Eligible patients for this study were men and women ≥35 years of age with chronic LBP who had a history of inadequate pain relief or intolerance to current analgesic therapy.

Inclusion Criteria: A patient must have met the following criteria to be eligible for inclusion in the study: (1) Male or female ≥35 years of age at the screening visit; (2) Provide signed informed consent; (3) Body mass index ≤39; (4) Clinical diagnosis of chronic moderate to severe LBP (non-radiculopathic) for ≥3 months (prior to the screening visit) as assessed by (a) Quebec taskforce category 1 (pain without radiation) or category 2 (pain with proximal radiation above the knee), (b) Primary pain location between 12th thoracic vertebra and lower gluteal fold (c) At both the screening and the randomization visit, an LBPI NRS score of ≥4 over the previous 24 hours, (d) During the pre-randomization period, mean daily LBPI score of ≥4, (e) At the screening visit, PGA of LBP of fair, poor or very poor; (5) History of regular analgesic medication, such as NSAIDs, COX-2 inhibitors, opioids, paracetamol/acetaminophen, or a combination thereof and includes (a) taking medication >4 days per week in the month prior to screening, (b) willing to discontinue current opioid pain medications starting at pre-randomization visit through the week 16 study visit, (c) willing to discontinue current NSAID pain medications (oral or topical) starting at pre-randomization visit through 16 weeks after last dose of study drug, (6) A history of inadequate pain relief or intolerance to analgesics used for chronic LBP as defined by: (a) Intolerance or inadequate pain relief from paracetamol/acetaminophen, and (b) Intolerance or inadequate pain relief from at least 1 oral NSAID, and (c) Intolerance or inadequate pain relief from at least 1 opioid, unwillingness to take opioid therapy or lack of access to opioid therapy; (7) Willing and able to comply with clinic visits and study-related procedures; (8) Able to understand and complete study-related questionnaires.

Exclusion Criteria: A patient who met any of the following criteria was excluded from the study: (1) Four or more consecutive LBPI NRS data entries missed during the pre-randomization period; (2) History of Quebec taskforce category >2 (pain with proximal radiation above the knee) lumbosacral radiculopathy within the past 2 years prior to the screening visit: (3) Evidence on baseline lumbar spine magnetic resonance imaging (MRI) (or lumbar spine X-ray, if requested) of moderate to severe spinal stenosis, disc herniation with substantial neural encroachment, recent vertebral fracture, an active destructive process or marked segmental instability (as indicated by bone marrow edema or Modic type I change, respectively); (4) History of major trauma, or back surgery in the past 6 months prior to the screening visit; (5) History of rheumatoid arthritis, multiple sclerosis, seronegative spondyloarthropathy, Paget's disease of the spine, pelvis, or femur, fibromyalgia, or tumors or infections of the spinal cord; (6) Use of extended-release opioids or long-acting opioids such as oxycodone controlled release, oxymorphone extended release, hydromorphone, transdermal fentanyl, or methadone within 3 months prior to the screening visit; (7) Use of a monoamine reuptake inhibitor, tricyclic antidepressants, selective serotonin reuptake inhibitors and serotonin norepinephrine reuptake inhibitors for treatment of pain within 4 weeks prior to the screening visit; (8) Systemic (ie, oral or intramuscular) corticosteroids or intra-articular corticosteroid injections within 30 days prior to the screening visit; (9) Epidural steroid injections within 3 months prior to the screening visit; (10) Botox injections for LBP within 6 months prior to the screening visit; (11) History or presence of subchondral insufficiency fracture or other evidence of destructive arthropathy on X-ray or MRI; (12) Is scheduled for a joint replacement surgery during the study period; (13) History or presence at the screening visit of autonomic neuropathy, diabetic neuropathy, or other peripheral neuropathy; (14) Evidence of autonomic neuropathy at the screening visit, as defined in the Survey of Autonomic Symptoms; (15) Poorly controlled diabetes (HbA1c >9.0%) at the screening visit; (16) Known history of human immunodeficiency virus infection; (17) Resting heart rate of <50 beats per minute (bpm) at the screening, pre-randomization or randomization visits; (18) History or presence of 2nd or 3rd degree heart block, 1st degree heart block with abnormal QRS, or bifascicular block by ECG at the screening visit; (19) History or presence of pyriformis syndrome; (20) History or presence of orthostatic hypotension at the screening or baseline visit; (21) Poorly controlled hypertension: (a) Systolic blood pressure ≥180 mm Hg or diastolic blood pressure ≥110 mm Hg at the screening visit; (b) Systolic blood pressure of 160 mm Hg to 179 mm Hg or diastolic blood pressure of 100 mm Hg to 109 mm Hg at the screening visit, AND a history of end-organ damage (including history of left ventricular hypertrophy, heart failure, angina, myocardial infraction, stroke, transient ischemic attack (TIA), peripheral arterial disease and moderate to advanced retinopathy [hemorrhages or exudates, papilledema]); (22) Congestive heart failure with NY Heart Classification of stage 3 or 4; (23) Myocardial infarction, acute coronary syndromes, TIA, or cerebrovascular accident within the past 12 months prior to the screening visit; (24) Significant concomitant illness including, but not limited to, psychiatric, cardiac, renal, hepatic, neurological, endocrinological, metabolic, or lymphatic disease that, in the opinion of the investigator, would adversely affect the patient's participation in the study; (25) New major illness diagnosed within 2 months prior to the screening visit; (26) Known history of infection with hepatitis B virus. Patients with a history of hepatitis B were eligible if there was documentation of a negative test for hepatitis B surface antigen and a positive test for antibodies to the hepatitis B virus surface antigen; (27) Known history of infection with hepatitis C virus. Patients with a history of hepatitis C were eligible if there was documentation of a negative hepatitis C virus RNA test; (28) History or presence of malignancy within the last 5 years prior to screening, except patients who were treated successfully with no recurrence for >1 year of basal cell or squamous cell carcinoma of the skin or in-situ cervical cancer; (29) Known allergy or sensitivity to doxycycline or related compounds, or monoclonal antibodies; (30) History of (within 5 years prior to the screening visit) current alcoholism, alcohol abuse, substance abuse, or abuse of prescription pain medication; (31) History of cannabis use for the treatment of pain within the past 6 months prior to the screening visit; (32) History of hospital admission for depression or suicide attempt within 5 years or active, severe major depression at screening; (33) Current or pending worker's compensation, litigation, disability, or any other monetary settlement related to LBP; (34) Ongoing participation in a clinical research study evaluating another investigational drug or having received another investigational product within 30 days or 5 half-lives, whichever is longer; (35) Exposure to an anti-NGF antibody within 6 months prior to the screening visit or known sensitivity or intolerance to anti-NGF antibodies; (36) Pregnant or breast-feeding women; (37) Women of childbearing potential who had a positive pregnancy test result or did not have their pregnancy test result at baseline; (38) Women of childbearing potential who were unwilling to use acceptable contraceptive methods during the study and for 20 weeks after the last dose of study drug. Acceptable methods of contraception include combined (estrogen and progesterone containing) hormonal contraception associated with inhibition of ovulation (oral, intravaginal, or transdermal); progesterone-only hormonal contraception associated with inhibition of ovulation (oral, injectable, or implantable); intrauterine device; intra-uterine hormone-releasing system; bilateral tubal occlusion; vasectomized partner; sexual abstinence; or condom in combination with either cap, diaphragm, or sponge with spermicide (double-barrier contraception).

Study Treatments

Patients were randomized to 1 of the following 4 treatment groups:

(a) Fasinumab 6 mg SC Q4W (every 4 weeks) and placebo 9 mg IV Q8W (every 8 weeks); (b) Fasinumab 9 mg SC Q4W and placebo 9 mg IV Q8W; (c) Fasinumab 9 mg IV Q8W and placebo 9 mg SC Q4W; (d) Placebo 6 mg or 9 mg SC Q4W and placebo 9 mg IV Q8W.

Patients randomized to treatment groups 1 or 2 (6 mg or 9 mg fasinumab) received SC injections of fasinumab on day 1, and at weeks 4, 8, and 12 for a total of 4 doses. These patients also received matching placebo IV on day 1 and at week 8. For patients randomized to SC administration, a loading dose equivalent to 2 times the maintenance dose was administered SC on day 1.

Patients randomized to treatment groups 3 or 4 received matching placebo to fasinumab SC, including the loading dose on day 1.

Patients randomized to treatment group 3 received IV infusions of fasinumab (9 mg) on day 1 and week 8) for a total of 2 doses. Patients randomized to treatment groups 1, 2, or 4 received matching placebo to fasinumab IV.

Study drug (fasinumab or placebo) was administered at the study site after all study visit procedures were completed. All SC injections were in the abdomen or thigh. At the day 1 and week 8 visits, patients received the SC injection first, followed by the IV infusion. After IV administration of study drug, patients were observed in the clinic for approximately 2 hours for evidence of a hypersensitivity reaction, and for 1 hour after SC dosing. Instructions for study drug administration were provided in the pharmacy manual. Doses of study drug were given within ±7 days from the scheduled dose date. If the window was missed, the dose was not administered. The next dose was administered at the next scheduled dosing date.

Rescue Treatment: Study-provided paracetamol/acetaminophen was the only allowable rescue medication for LBP during the study from pre-randomization visit through end of treatment (week 16).

Method of Treatment Assignment

Approximately 563 patients were randomized in a 1:1:1:1 ratio to 1 of the 4 treatment groups according to a predetermined central randomization scheme generated and provided to study site personnel by the interactive voice response system (IVRS). Randomization was stratified by baseline LBPI NRS score, duration of chronic LBP, and maximum K-L score at any knee or hip joint at screening.

Study patients, the principal investigators, and study site personnel remained blinded to all randomization assignments throughout the study, unless unblinding was necessary due to a medical emergency, or due to any other significant medical event (e.g. pregnancy).

Population of Analysis

The modified intent-to treat (MITT) set includes all randomized patients who received any study drug. Analysis based on the MITT includes data up to 5 weeks after the last dose of study drug for patients included in the analysis set. Efficacy endpoints were analyzed using the MITT set.

The full analysis set (FAS) includes all randomized patients and it is based on the treatment allocated (as randomized). Efficacy endpoints were also analyzed using the FAS.

The safety analysis set (SAF) includes all randomized patients who received any study drug; it is based on the treatment received (as treated). Treatment compliance/administration and all clinical safety variables were analyzed using the SAF.

Concomitant Therapy

Any treatment administered from screening until the end of study (week 36) was considered concomitant medication. This included medications that were started prior to the study and were ongoing during the study.

Permitted Therapy: Patients receiving chronic medication therapy must have been on a stable dose of such medication for at least the 30 days prior to the screening visit. Monoamine reuptake inhibitors were permitted for nonpain related treatment, as were tricyclic antidepressants, selective serotonin reuptake inhibitors and serotonin norepinephrine reuptake inhibitors. Patients must have been on therapy for at least 8 consecutive weeks and on a stable dose for at least 4 weeks prior to the screening visit and throughout the planned duration of the patient's participation in the study.

Low-dose aspirin (up to 100 mg/day) for cardiac prophylaxis was also permitted. Paracetamol/acetaminophen taken acutely for treatment of non-LBP was also permitted. Paracetamol/acetaminophen taken for non-LBP relief was reported as concomitant medication. Other permitted medications were glucosamine, chondroitin sulfate, and rescue medications. Topical steroids and topical non-NSAID analgesics were also permitted.

Physical therapy and chiropractic or alternative therapy (such as acupuncture) were permitted if their use was stable for the month preceding the screening visit and was expected to remain stable for the duration of the study.

Prohibited Therapy: Patients who met the initial eligibility criteria at the screening visit were asked to discontinue their current NSAID (oral or topical; except up to 100 mg/day of aspirin, which was permitted for cardiac prophylaxis) and opioid analgesic medications, starting at the pre-randomization visit.

Opioid analgesic medications (including tramadol) were prohibited through the week 16 study visit. Patients were directed not to take concomitant medications that contain NSAIDs (oral or topical, except up to 100 mg/day of aspirin, which was permitted for cardiac prophylaxis) until at least 16 weeks after the last dose of study drug. A list of medications containing NSAIDs was provided in the study reference manual.

Other excluded drugs were: Any other investigational agent; Cyclosporine; Azathioprine; Medical marijuana; Tumor necrosis factor antagonists; Corticosteroids (topical and inhaled formulations are permitted); Tocilizumab; Abatacept; Cyclobenzaprine, carisoprodol, orphenadrine, tizanidine; Muscle relaxants.

Study Procedures

Study assessments and procedures are presented by study period and visit in FIGS. 1 and 2. A schedule for follow-up of TJR surgery during the study is shown in FIG. 3. Procedures performed only at the screening visit, pre-randomization visit, or baseline/randomization visit are shown below.

Informed Consent: All patients must have signed and dated an Institutional Review Board (IRB)-approved or Ethics Committee (EC)-approved informed consent form (ICF) before any study procedures were performed.

Medical History: The investigator or designee took a complete medical history that included information on concurrent medical conditions and the severity for each condition that had not resolved.

Medication History: The investigator or designee queried patients on the medication(s) they took (medication history), including information on their ability to tolerate the medication, and recorded the information on an eCRF for this purpose.

Assessment of Childbearing Potential: Each female patient was evaluated for childbearing potential. Women were considered to be of childbearing potential unless: they were postmenopausal, or they had a tubal ligation, a bilateral oophorectomy, bilateral salpingectomy, or hysterectomy. In women ≥59 years of age, postmenopausal is defined as at least 12 continuous months of spontaneous amenorrhea. In women ≤59 years of age, postmenopausal is defined as at least 12 continuous months of spontaneous amenorrhea, with serum follicle-stimulating hormone (FSH) levels >40 IU/L and serum estradiol levels <5 ng/dL.

EDiary Training: When initial patient eligibility had been determined during the screening period, patients returned to the site for a pre-randomization visit. At this visit, patients were instructed on the use of the NRS for scoring their LBP pain, and they were trained on the EDiary to report their LBP NRS score and their daily paracetamol/acetaminophen use for LB pain.

Assessment of Peripheral vs. Central Pain: Patients completed the Assessment of Peripheral vs. Central Pain, a self-reported survey, to evaluate the peripheral versus central nature of their pain at certain time points.

Assessment of Neuropathic vs. Nociceptive Pain: Patients completed the painDETECT questionnaire to evaluate the neuropathic versus nociceptive nature of their pain at the time points indicated. The questionnaire was self-administered and consisted of 7 questions that addressed the quality of neuropathic pain symptoms. The first 5 questions asked about the gradation of pain on a 6-point Likert scale (0=never; 1=hardly noticed; 2=slightly; 3=moderately; 4=strongly; 5=very strongly). Question 6 asked about the pain course pattern (scored from −1 to 2), and question 7 asked about radiating pain, answered 'yes' or 'no' (scored as 0 or 2, respectively).

Efficacy Procedures

Daily Low Back Pain Intensity Numerical Rating Score (LBPI NRS): At the screening visit and the pre-randomization visit, the investigator or designee entered the LBPI NRS score indicating pain over the past 24 hours into the electronic case report form (eCRF) based on the patient's report. Once initial eligibility was confirmed, from the pre-randomization visit to the week 16 study visit, LBPI NRS scores were reported by the patient into the EDiary every day at approximately 6 PM. A copy of the assessment was provided in the study reference manual.

Roland Morris Disability Questionnaire (RMDQ): The RMDQ is a self-administered, widely used health status measure for LBP (Roland, M. O. et. al., (1983), Spine 8:141-144). It measures pain and function, using 24 items describing limitations to everyday life that can be caused by LBP. The score of the RMDQ is the total number of items checked—ie, from a minimum of 0 to a maximum of 24. Patients completed the questionnaire at the time points indicated.

Patient Global Assessment of Low Back Pain (PGA of LBP): The PGA of LBP is a patient-rated assessment of their current disease state on a 5-point Likert scale (1=very well; 2=well; 3=fair; 4=poor; and 5=very poor). Patients completed the assessment scale at the time points indicated.

Short Form (36) Health Survey (SF-36): The SF-36 is a self-administered survey of general health. It measures 8 domains of health: physical functioning, role limitations due to physical health, bodily pain, general health perceptions, vitality, social functioning, role limitations due to emotional problems, and mental health. It yields scale scores for each of these 8 health domains, and 2 summary measures of physical and mental health: the physical component summary and the mental component summary. Patients completed the survey at the time points indicated.

Medical Outcomes Study Sleep Survey (MOS): The MOS Sleep Survey is a self-administered 12-question survey of sleep habits (Hays, R. D. (1992), Sleep Measures. In A. L. Stewart & J. E. Ware (eds.), Measuring functioning and well being: The Medical Outcomes Study approach (pp 235-259), Durham, N.C.: Duke University Press). Patients completed the questionnaire at the time points indicated.

EQ-5D-5L: The EQ-5D-5L is a standardized measure of health status developed by the EuroQol Group to provide a simple, generic measure of health for clinical and economic appraisal. The EQ-5D-5L, as a measure of health-related quality of life, defines health in terms of 5 dimensions: mobility, self-care, usual activities, pain/discomfort, anxiety/depression. Each dimension has 3 ordinal levels of severity: "no problem" (1), "some problems" (2), "severe problems" (3). Overall health state is defined as a 5-digit number. Health states defined by the 5-dimensional classification can be converted into corresponding index scores that quantify health status, where −0.594 represents "severe problems" and 1 represents "no problem." Patients completed the questionnaire at the time points indicated.

Safety Procedures

Physical Examination: Patients had a thorough and complete physical examination including an examination of the knees, hips, and shoulders at the time points indicated. Care was taken to examine and assess any abnormalities that may be present, as indicated by the patient's medical history. Measurements of patient height and weight were recorded at the time points indicated.

Vital Signs: Vital signs including temperature, sitting blood pressure, pulse, and respiration were collected at the time points indicated. Pulse was measured over a 1-minute period. At visits at which study drug was administered, vital signs were measured before administration of the study drug. If the pulse was less than 45 bpm, an ECG with rhythm strip was obtained to confirm the heart rate and rhythm.

Electrocardiogram: A standard 12-lead ECG was performed at the time points indicated. Heart rate was recorded from the ventricular rate and the PR, QRS, and QT, QTc intervals were recorded. The ECG data was read by a central reading center.

Joint Pain Questionnaire: A joint pain questionnaire was completed by the patient at the time points indicated. For each knee, hip, and shoulder joint, the patient was prompted to indicate if they have experienced pain.

Survey of Autonomic Symptoms: Signs and symptoms of autonomic dysfunction were assessed by the investigator at the time points indicated.

Assessment of Orthostatic Blood Pressure: An assessment of orthostatic blood pressure was conducted at the time points indicated. Orthostatic hypotension is defined as a decrease in systolic blood pressure of 20 mm Hg or a decrease in diastolic blood pressure of 10 mm Hg within 3 minutes of standing when compared with blood pressure from the supine position (Kaufmann, H. (1996), Clin Auton Res 6125-6126).

Neurological Evaluation: A full or a brief neurological examination was performed at the time points indicated. Neurological findings at baseline that were not exclusionary were recorded in medical history. Findings at subsequent visits were assessed by the investigator to determine if these should be recorded as an AE. The neurological examination covered the following domains: motor, sensory, cranial nerves, reflexes, and coordination/balance and were conducted by any clinician at the site qualified to do so. Whenever possible, the same clinician who conducted the baseline neurological examination continued to conduct the examinations on a given patient. The investigator referred patients with persistent or worsening neurologic symptoms for a neurologic consultation, if clinically indicated.

Imaging: Radiographs of the large joints (knees, hips, and shoulders) were taken using a standard approach at the time points indicated. An MRI of any hip or knee joint with a baseline K-L score of ≥3 at screening was conducted. In addition, radiographs and/or an MRI was performed of any joint following a report of clinically significant worsening or exacerbation of pain in that joint.

Radiographs: Weight-bearing (standing) posterior-anterior radiographs of both knees in the semi-flexed position, and anterior-posterior radiographs of both hips and both shoulders, was conducted. Radiographs of the knees, hips, and shoulders were sent to a central reader, and evaluated to confirm no evidence of destructive arthropathy, subchondral insufficiency fracture, or osteonecrosis.

MRI: An MRI of the lumbar spine was taken using standard Acquisition Sequences at the time point indicated to assess for evidence of the following: disc degeneration or herniation, disc signal and height loss, Modic endplate changes, bone marrow edema, central subarticular or foraminal stenosis, spondylolisthesis, spondylolysis, and facet joint arthropathy. If the MRI suggested a destructive or unstable spinal process, flexion/extension radiographs were requested. An MRI of any hip or knee joint with a baseline K-L score ≥3 was acquired at the time points indicated. Prior to subject randomization, MRIs were sent to a central reader and evaluated to confirm no evidence of destructive arthropathy or other exclusionary features.

Procedures to be Performed Only in the Event of a Total Joint Replacement (TJR) Surgery In the event that a patient had to undergo TJR surgery during the study, the patient completed the early termination visit (week 16 or week 36 assessments as outlined and the procedures outlined in the schedule of events for TJR surgery follow-up). The early termination visit was to be completed before TJR surgery if at all possible. All pain patient-reported outcomes should have been completed before the physical examination.

In the event that the early termination visit was not performed pre-operatively, standard of care pre-operative images of the joint with TJR were obtained and submitted to the central imaging vendor. Imaging of all other joints per early termination visit procedures were done post-operatively at the first TJR follow-up study visit if not done before surgery.

Knee Society Score: The Knee Society Score is an investigator-completed questionnaire that is used to objectively measure a patient's ability to function before and after total knee arthroplasty (Insall, J. N. et al., (1989) Clin Ortho Relat Res Nov (24*):13-14.

Harris Hip Score: The Harris Hip Score is an investigator-completed questionnaire that is used to objectively measure a patient's ability to function before and after total hip arthroplasty Harris, W. H., et al., (1969), J Bone Joint Surg Am Jun; 51(4):737-755).

Laboratory Testing: The central laboratory analyzed all screening and on-study laboratory samples for blood chemistry, hematology, HbA1c, urine analysis, and serum pregnancy. Urine pregnancy testing was done at the site using kits provided by the central laboratory.

Other Laboratory Tests: Serum and urine samples for pregnancy testing were collected from women of childbearing potential. At dosing study visits, urine pregnancy testing were done before the study drug was administered. In the event of a positive urine pregnancy test result, the patient would have a serum pregnancy test with a negative result in order to continue study participation.

To assess postmenopausal status for women ≤59 years of age, serum samples to test for FSH levels and estradiol levels were collected for analysis at the central laboratory.

Abnormal Laboratory Values and Laboratory Adverse Events: All laboratory values were reviewed by the investigator or authorized designee. Significantly abnormal tests were repeated to confirm the nature and degree of the abnormality.

The clinical significance of an abnormal test value, within the context of the disease under study, was determined by the investigator.

Pharmacokinetic and Antibody Procedures

Drug Concentration and Anti-Drug Antibody Measurements: Serum and plasma samples for measuring drug concentration were collected and any unused samples collected for drug concentration measurements were used for exploratory biomarker research or to investigate unexpected AEs. Samples were tested for anti-drug antibody measurements.

Safety Assessment

Safety was assessed throughout the study by monitoring Adverse Events (AEs) and Serious Adverse Events (SAEs).

An Adverse Event is any untoward medical occurrence in a patient administered a study drug, which may or may not have a causal relationship with the study drug. An AE can, therefore, be any unfavorable and unintended sign (including abnormal laboratory finding), symptom, or disease temporally associated with the use of a study drug, whether or not considered related to the study drug.

AEs also include: any worsening (i.e., any clinically significant change in frequency and/or intensity) of a pre-existing condition that is temporally associated with the use of the study drug.

A Serious Adverse Event is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event. All SAEs were reported to the sponsor within 24 hours.

In addition, laboratory safety variables, vital sign variables, 12-lead electrocardiography (ECG) variables, and physical examination variables were measured throughout the study. These have been noted above.

Monitoring Adverse Events of Special Interest

Destructive Arthropathy: Potential events of destructive arthropathy were monitored via clinical signs and symptoms of new or worsening joint pain during the course of the study (e.g., by applying the joint pain questionnaire, physical examination, and imaging). Clinically significant new or worsening joint pain during the course of this study is defined as worsening of pain in any joint despite treatment with analgesics and that lasts at least 2 weeks (or less at the discretion of the investigator). If a patient reported such an increase in pain in any joint then study drug administration was withheld and the patient was evaluated by the principal investigator. Imaging of the affected joint, as well as any additional imaging deemed appropriate to understand the cause of the worsening pain, was performed. Patients with findings that suggest destructive arthropathy had their dosing terminated and were referred for orthopedic consultation.

Sympathetic Nervous System Dysfunction: Sympathetic nervous dysfunction was monitored throughout the study through the Survey of Autonomic Symptoms). New onset or worsening of signs and symptoms of autonomic dysfunction were evaluated by the investigator. In cases where new or worsening symptoms were moderate to severe or were clinically-significant and did not resolve or return to baseline in 2 weeks (or less at the discretion of the investigator), study drug was withheld and the patient was referred to a specialist. Study drug was permanently discontinued for any one of the following: (a) Evidence of sympathetic dysfunction in the opinion of the specialist; (b) A confirmed heart rate below 45 bpm; (c) New onset heart block; (d) Syncope where there is no obvious etiology; (e) Orthostatic hypotension.

Study Variables

Baseline characteristics included standard demography (eg, age, race, weight, height, etc), disease characteristics including baseline LBPI NRS score, duration of chronic back pain, maximum K-L score at any knee or hip joint at screening, use of paracetamol/acetaminophen as rescue medication during the pre-randomization period, medical history, and medication history for each patient.

Primary and Secondary Endpoints: The primary endpoint in the study was the change from baseline at week 16 in the average daily LBPI NRS score.

Secondary endpoints: The secondary endpoints were (1) Change from baseline at week 16 in the RMDQ total score; (2) Change from baseline at week 16 in the PGA of LBP score; (3) Change from baseline at weeks 2, 4, 8, and 12 in the LBPI NRS score.

Safety endpoints: (1) Percent of patients reporting TEAEs; (2) The incidence of anti-fasinumab antibody formation.

Exploratory Endpoints: The change from baseline at week 16 in the percentage of patients who were responders defined by 30% reduction and 50% reduction for: (1) average daily LBPI NRS score; (2) RMDQ total score; (3) PGA of LBP score; (4) Change from baseline at week 16 in the MOS sleep subscale score; (5) Change from baseline at week 16 in the SF-36 subscale scores; (6) Change from baseline at week 16 in the EQ-5D-5L; (7) Change from baseline at week 16 in the percentage of patients who use rescue medication from LBP.

Pharmacokinetic Variables: The PK variables may include, but are not limited to, serum concentration of fasinumab at scheduled time points.

Anti-drug Antibody Variables: Samples for ADA evaluation were collected at baseline and subsequent study visits.

Efficacy Analyses

Primary Efficacy Analysis: The statistical tests were 2-sided at the 0.05 significance level. The primary efficacy variables were analyzed using a mixed-effect model repeated measure (MMRM) approach. The model included the randomization strata, relevant baseline, treatment, visit, and treatment-by-visit interaction. The least-squares means estimates for the mean change from baseline to week 16, as well as the differences of the estimates between fasinumab doses and placebo, with their corresponding standard errors, p-values and associated 95% confidence intervals, were provided from the MMRM model. Sensitivity analyses was performed the same way for the primary and selected secondary endpoints using the PPS.

Secondary Efficacy Analysis: Tests were performed at the 2-sided, 5% significance level without multiplicity adjustment. For analysis of continuous variables in secondary endpoints, the analysis method was the same as for the primary variables. For analysis of categorical variables in secondary endpoints, the Cochran-Mantel-Haenszel approach stratified by the randomization strata was used.

Safety Analysis

The safety analysis was based on the reported AEs, clinical laboratory evaluations and vital signs. The time interval to detect any event or abnormality was between the infusion of study medication and end of study. Data collected outside this interval were excluded from the calculation of descriptive statistics and identification of abnormalities for laboratory evaluations and vital signs.

Adverse Events: Treatment-emergent adverse events (TEAEs) are defined as those that are not present at baseline or which represent the exacerbation of a preexisting condition during the on-treatment period. All AEs reported in this study were coded using the currently available version of the Medical Dictionary for Regulatory Activities (MedDRA®). Coding was to lowest level terms. The verbatim text, the preferred term (PT), and the primary system organ class (SOC) was listed.

Vital signs: (temperature, pulse, blood pressure and respiration rate) was summarized by baseline and change from baseline to each scheduled assessment time with descriptive statistics.

Laboratory test results: was summarized by baseline and change from baseline to each scheduled assessment time with descriptive statistics.

Results

Subject Accountability

Table 2 summarizes the data sets that were analyzed. Five randomized patients did not receive any study drug and were excluded from the safety analysis and the efficacy analysis using the MITT analysis set.

TABLE 2

Data Sets Analyzed

| Patient Population | Placebo | 6 mg SC | 9 mg SC | 9 mg IV | All R475 | Total |
|---|---|---|---|---|---|---|
| Full Analysis Set (FAS) | 141 | 141 | 140 | 141 | 422 | 563 |
| Modified Intent to Treat Analysis Set (MITT) | 140 | 139 | 139 | 140 | 418 | 558 |
| Safety Analysis Set (SAF) | 140 | 139 | 139 | 140 | 418 | 558 |

Study Disposition

Approximately 30% (166/563) of the randomized patients had completed the last visit in the treatment phase (Week 16 visit) at the time of this analysis. Among these, 6 patients had discontinued study treatment early due to an adverse event (3 patients), physician decision (2 patients) and subject withdrawal (1 patient). Table 3 summarizes the subject disposition.

TABLE 3

Summary of Subject Disposition - FAS

| | Placebo (N = 141) | Fasinumab 6 mg SC Q4W (N = 141) | Fasinumab 9 mg SC Q4W (N = 140) | Fasinumab 9 mg IV Q8W (N = 141) | Combined (N = 422) | Total (N = 563) |
|---|---|---|---|---|---|---|
| Patients randomized | 141 | 141 | 140 | 141 | 422 | 563 |
| Randomized patients who received at least 1 dose of study medication | 140 (99.3%) | 139 (98.6%) | 139 (99.3%) | 140 (99.3%) | 418 (99.1%) | 558 (99.1%) |
| Randomized patients who completed the week 16 visit before the FDA hold | 39 (27.7%) | 40 (28.4%) | 42 (30.0%) | 45 (31.9%) | 127 (30.1%) | 166 (29.5%) |
| Discontinued treatment early? | | | | | | |
| No | 38 (27.0%) | 39 (27.7%) | 40 (28.6%) | 43 (30.5%) | 122 (28.9%) | 160 (28.4%) |

TABLE 3-continued

Summary of Subject Disposition - FAS

|  | Placebo (N = 141) | Fasinumab 6 mg SC Q4W (N = 141) | Fasinumab 9 mg SC Q4W (N = 140) | Fasinumab 9 mg IV Q8W (N = 141) | Combined (N = 422) | Total (N = 563) |
|---|---|---|---|---|---|---|
| Yes | 1 (0.7%) | 1 (0.7%) | 2 (1.4%) | 2 (1.4%) | 5 (1.2%) | 6 (1.1%) |
| Primary reason for treatment discontinuation |  |  |  |  |  |  |
| Adverse event | 0 | 0 | 2 (1.4%) | 1 (0.7%) | 3 (0.7%) | 3 (0.5%) |
| Physician decision | 0 | 1 (0.7%) | 0 | 1 (0.7%) | 2 (0.5%) | 2 (0.4%) |
| Withdrawal by subject | 1 (0.7%) | 0 | 0 | 0 | 0 | 1 (0.2%) |
| Randomized patients who did not complete the week 16 visit before the FDA hold | 102 (72.3%) | 101 (71.6%) | 98 (70.0%) | 96 (68.1%) | 295 (69.9%) | 397 (70.5%) |
| Discontinued study early? |  |  |  |  |  |  |
| No | 60 (42.6%) | 68 (48.2%) | 76 (54.3%) | 73 (51.8%) | 217 (51.4%) | 277 (49.2%) |
| Yes | 42 (29.8%) | 33 (23.4%) | 22 (15.7%) | 23 (16.3%) | 78 (18.5%) | 120 (21.3%) |
| Primary reason for early study termination |  |  |  |  |  |  |
| Adverse event | 8 (5.7%) | 4 (2.8%) | 3 (2.1%) | 4 (2.8%) | 11 (2.6%) | 19 (3.4%) |
| Death | 0 | 1 (0.7%) | 0 | 0 | 1 (0.2%) | 1 (0.2%) |
| Lost to follow-up | 4 (2.8%) | 7 (5.0%) | 1 (0.7%) | 4 (2.8%) | 12 (2.8%) | 16 (2.8%) |
| Physician decision | 7 (5.0%) | 3 (2.1%) | 3 (2.1%) | 4 (2.8%) | 10 (2.4%) | 17 (3.0%) |
| Protocol deviation | 4 (2.8%) | 2 (1.4%) | 1 (0.7%) | 1 (0.7%) | 4 (0.9%) | 8 (1.4%) |
| Withdrawal by subject | 19 (13.5%) | 16 (11.3%) | 14 (10.0%) | 10 (7.1%) | 40 (9.5%) | 59 (10.5%) |

Dosage and Duration

Table 4 summarizes the duration of exposure to both SC study drug administration and IV drug administration.

TABLE 4

Summary of Treatment Duration-FAS

|  | Placebo (N = 140) | Fasinumab 6 mg SC Q4W (N = 139) | Fasinumab 9 mg SC Q4W (N = 139) | Fasinumab 9 mg IV Q8W (N = 140) | Combined (N = 418) | Total (N = 558) |
|---|---|---|---|---|---|---|
| SC Study Drug Injection |  |  |  |  |  |  |
| Duration of treatment (days) |  |  |  |  |  |  |
| n | 140 | 139 | 139 | 140 | 418 | 558 |
| Mean (SD) | 75.0 (33.95) | 75.0 (33.77) | 76.9 (34.55) | 76.9 (34.77) | 76.3 (34.30) | 76.0 (34.18) |
| Median | 82.0 | 83.0 | 83.0 | 84.0 | 83.0 | 83.0 |
| Q1:Q3 | 49.5:110.0 | 49.0:111.0 | 49.0:111.0 | 49.0:112.0 | 49.0:112.0 | 49.0:112.0 |
| Min:Max | 28:124 | 28:122 | 28:119 | 28:120 | 28:122 | 28:124 |

TABLE 4-continued

Summary of Treatment Duration-FAS

| | Placebo (N = 140) | Fasinumab | | | | Total (N = 558) |
| --- | --- | --- | --- | --- | --- | --- |
| | | 6 mg SC Q4W (N = 139) | 9 mg SC Q4W (N = 139) | 9 mg IV Q8W (N = 140) | Combined (N = 418) | |
| Duration of treatment by category, n(%) | | | | | | |
| >=1 Day to <29 Days | 33 (23.6%) | 32 (23.0%) | 33 (23.7%) | 34 (24.3%) | 99 (23.7%) | 132 (23.7%) |
| >=29 Days to <57 Days | 21 (15.0%) | 29 (20.9%) | 18 (12.9%) | 20 (14.3%) | 67 (16.0%) | 88 (15.8%) |
| >=57 Days to <85 Days | 26 (18.6%) | 18 (12.9%) | 26 (18.7%) | 19 (13.6%) | 63 (15.1%) | 89 (15.9%) |
| >=85 Days | 60 (42.9%) | 60 (43.2%) | 62 (44.6%) | 67 (47.9%) | 189 (45.2%) | 249 (44.6%) |
| Number of SC injections | | | | | | |
| 1 | 33 (23.6%) | 32 (23.0%) | 33 (23.7%) | 34 (24.3%) | 99 (23.7%) | 132 (23.7%) |
| 2 | 33 (23.6%) | 32 (23.0%) | 28 (20.1%) | 28 (20.0%) | 88 (21.1%) | 121 (21.7%) |
| 3 | 23 (16.4%) | 26 (18.7%) | 19 (13.7%) | 22 (15.7%) | 67 (16.0%) | 90 (16.1%) |
| 4 | 51 (36.4%) | 49 (35.3%) | 59 (42.4%) | 56 (40.0%) | 164 (39.2%) | 215 (38.5%) |
| IV Study Drug Infusion Duration of treatment (days) | | | | | | |
| n | 140 | 138 | 139 | 140 | 417 | 557 |
| Mean (SD) | 84.5 (27.96) | 85.0 (28.38) | 87.3 (27.90) | 86.4 (28.13) | 86.3 (28.09) | 85.8 (28.04) |
| Median | 105.0 | 105.0 | 107.0 | 106.0 | 106.0 | 105.0 |
| Q1:Q3 | 56.0:112.0 | 56.0:112.0 | 56.0:112.0 | 56.0:112.0 | 56.0:112.0 | 56.0:112.0 |
| Min:Max | 56:119 | 56:119 | 56:119 | 56:120 | 56:120 | 56:120 |
| Duration of treatment by category, n(%) | | | | | | |
| >=1 Day to <29 Days | 0 | 0 | 0 | 0 | 0 | 0 |
| >=29 Days to <57 Days | 68 (48.6%) | 67 (48.2%) | 61 (43.9%) | 64 (45.7%) | 192 (45.9%) | 260 (46.6%) |
| >=57 Days to <85 Days | 0 | 0 | 0 | 0 | 0 | 0 |
| >=85 Days | 72 (51.4%) | 71 (51.1%) | 78 (56.1%) | 76 (54.3%) | 225 (53.8%) | 297 (53.2%) |
| Number of IV injections | | | | | | |
| 1 | 68 (48.6%) | 67 (48.2%) | 61 (43.9%) | 64 (45.7%) | 192 (45.9%) | 260 (46.6%) |
| 2 | 72 (51.4%) | 71 (51.1%) | 78 (56.1%) | 76 (54.3%) | 225 (53.8%) | 297 (53.2%) |
| Missing | 0 | 1 | 0 | 0 | 1 | 1 |

The duration of exposure to both SC drug administration and IV drug administration was similar between the placebo group and the fasinumab treated groups.

Baseline Characteristics

Patients had a mean duration of chronic low back pain of 13 years and a baseline low back pain intensity numerical rating score of 6.53. The majority of patients had maximum Kellgren-Lawrence scores of 1 or 2. Randomization stratification factors and baseline disease characteristics were generally balanced across treatment groups. A summary of the baseline characteristics is shown in Table 5.

TABLE 5

Summary of Baseline Characteristics - FAS

|  | Placebo (N = 141) | Fasinumab | | | | Total (N = 563) |
|---|---|---|---|---|---|---|
|  |  | 6 mg SC Q4W (N = 141) | 9 mg SC Q4W (N = 140) | 9 mg IV Q8W (N = 141) | Combined (N = 422) |  |
| LBPI NRS baseline score | | | | | | |
| n | 140 | 139 | 140 | 141 | 420 | 560 |
| Mean (SD) | 6.50 (1.297) | 6.49 (1.281) | 6.66 (1.300) | 6.45 (1.191) | 6.53 (1.258) | 6.53 (1.267) |
| Median | 6.60 | 6.50 | 6.60 | 6.60 | 6.60 | 6.60 |
| Q1:Q3 | 5.60:7.40 | 5.60:7.40 | 5.80:7.50 | 5.60:7.40 | 5.71:7.40 | 5.60:7.40 |
| Min:Max | 3.8:9.8 | 3.2:10.0 | 3.6:9.8 | 3.4:9.6 | 3.2:10.0 | 3.2:10.0 |
| LBPI NRS baseline score strata, n (%) | | | | | | |
| <7 | 63 (44.7%) | 63 (44.7%) | 63 (44.3%) | 64 (45.4%) | 189 (44.8%) | 252 (44.8%) |
| >=7 | 78 (55.3%) | 78 (55.3%) | 78 (55.7%) | 77 (54.6%) | 233 (55.2%) | 311 (55.2%) |
| Duration of chronic back pain at baseline (years) | | | | | | |
| n | 126 | 131 | 135 | 134 | 400 | 526 |
| Mean | 11.835 | 13.645 | 13.688 | 12.680 | 13.336 | 12.977 |
| (SD) | (10.1768) | (12.1044) | (13.0152) | (10.6728) | (11.9505) | (11.5589) |
| Median | 8.665 | 9.730 | 10.300 | 8.590 | 9.565 | 9.330 |
| Q1:Q3 | 4.210:16.460 | 4.420:20.670 | 4.690:18.450 | 4.780:18.540 | 4.690:20.015 | 4.630:17.690 |
| Min:Max | 0.51:46.34 | 0.45:53.63 | 0.28:72.74 | 0.59:52.40 | 0.28:72.74 | 0.28:72.74 |
| Duration of chronic back pain baseline strata n (%) | | | | | | |
| <5 years | 41 (29.1%) | 41 (29.1%) | 39 (27.9%) | 40 (28.4%) | 120 (28.4%) | 161 (28.6%) |
| >=5 years | 100 (70.9%) | 100 (70.9%) | 101 (72.1%) | 101 (71.6%) | 302 (71.6%) | 402 (71.4%) |
| Maximum Kellgren-Lawrence score at any knee or hip joint at screening, n(%) | | | | | | |
| 0 | 25 (17.7%) | 16 (11.3%) | 35 (25.0%) | 25 (17.7%) | 76 (18.0%) | 101 (17.9%) |
| 1 | 51 (36.2%) | 49 (34.8%) | 35 (25.0%) | 43 (30.5%) | 127 (30.1%) | 178 (31.6%) |
| 2 | 40 (28.4%) | 52 (36.9%) | 42 (30.0%) | 50 (35.5%) | 144 (34.1%) | 184 (32.7%) |
| 3 | 21 (14.9%) | 21 (14.9%) | 23 (16.4%) | 18 (12.8%) | 62 (14.7%) | 83 (14.7%) |
| 4 | 4 (2.8%) | 3 (2.1%) | 5 (3.6%) | 5 (3.5%) | 13 (3.1%) | 17 (3.0%) |
| Use of rescue medication during pre-randomization period (Paracetamol/Acetaminophen), n (%) | | | | | | |
| Yes | 16 (11.3%) | 22 (15.6%) | 22 (15.7%) | 21 (14.9%) | 65 (15.4%) | 81 (14.4%) |
| No | 125 (88.7%) | 119 (84.4%) | 118 (84.3%) | 120 (85.1%) | 357 (84.6%) | 482 (85.6%) |

TABLE 5-continued

Summary of Baseline Characteristics - FAS

| | Placebo (N = 141) | Fasinumab 6 mg SC Q4W (N = 141) | Fasinumab 9 mg SC Q4W (N = 140) | Fasinumab 9 mg IV Q8W (N = 141) | Combined (N = 422) | Total (N = 563) |
|---|---|---|---|---|---|---|
| Presence of a neuropathic pain component, n (%) | | | | | | |
| Positive | 18 (12.8%) | 20 (14.2%) | 24 (17.1%) | 22 (15.6%) | 66 (15.6%) | 84 (14.9%) |
| Unclear | 31 (22.0%) | 29 (20.6%) | 18 (12.9%) | 30 (21.3%) | 77 (18.2%) | 108 (19.2%) |
| Negative | 92 (65.2%) | 91 (64.5%) | 98 (70.0%) | 89 (63.1%) | 278 (65.9%) | 370 (65.7%) |

Efficacy Results

Primary Efficacy Endpoint

Table 6 summarizes the results of the primary efficacy endpoint. The primary endpoint results are also shown in FIG. 4.

TABLE 6

Summary of change from baseline to Week 8 and 16 in the LBPI NRS score (score range: 0 to 10) - MITT (Modified Intent To Treat set)

| Week Average daily LBPI NRS score Change from Baseline | Placebo (N = 140) | Fasinumab 6 mg SC Q4W (N = 139) | Fasinumab 9 mg SC Q4W (N = 139) | Fasinumab 9 mg IV Q8W (N = 140) |
|---|---|---|---|---|
| Baseline Average daily LBPI NRS score | | | | |
| n | 139 | 137 | 139 | 140 |
| Mean (SD) | 6.52 (1.287) | 6.48 (1.288) | 6.67 (1.297) | 6.44 (1.184) |
| Median | 6.60 | 6.40 | 6.60 | 6.50 |
| Q1:Q3 | 5.60:7.40 | 5.60:7.40 | 5.80:7.50 | 5.60:7.33 |
| Min:Max | 3.8:9.8 | 3.2:10.0 | 3.6:9.8 | 3.4:9.6 |
| Week 8 Average daily LBPI NRS score | | | | |
| n | 96 | 99 | 105 | 103 |
| Mean (SD) | 5.33 (2.092) | 4.67 (1.985) | 4.26 (2.379) | 4.10 (2.343) |
| Median | 5.38 | 4.86 | 4.29 | 4.14 |
| Q1:Q3 | 4.00:7.00 | 3.14:6.29 | 2.43:6.14 | 2.14:6.00 |
| Min:Max | 0.1:9.0 | 0.4:9.0 | 0.0:9.3 | 0.0:9.3 |
| Change from baseline to week 8 | | | | |
| n | 95 | 98 | 105 | 103 |
| Mean (SD) | −1.26 (1.795) | −1.86 (1.923) | −2.42 (2.172) | −2.26 (2.240) |
| Median | −1.06 | −1.41 | −2.11 | −2.00 |
| Q1:Q3 | −2.00:−0.11 | −3.40:−0.33 | −4.11:−0.80 | −4.00:−0.46 |
| Min:Max | −6.0:3.9 | −7.4:1.2 | −7.5:2.7 | −8.4:2.4 |
| LS Mean (SE) | −1.2 (0.19) | −1.8 (0.19) | −2.3 (0.19) | −2.2 (0.19) |
| 95% CI | (−1.61, −0.84) | (−2.15, −1.39) | (−2.66, −1.91) | (−2.58, −1.83) |
| Difference vs. Placebo LS Mean (SE) | | −0.5 (0.26) | −1.1 (0.26) | −1.0 (0.26) |
| 95% CI | | (−1.06, −0.03) | (−1.57, −0.55) | (−1.48, −0.47) |
| Week 16 Average daily LBPI NRS score | | | | |
| n | 50 | 48 | 55 | 56 |
| Mean (SD) | 4.66 (2.045) | 4.31 (1.864) | 4.21 (2.273) | 3.92 (2.426) |
| Median | 5.00 | 4.42 | 4.00 | 3.86 |
| Q1:Q3 | 3.50:6.00 | 3.00:5.24 | 2.00:5.83 | 2.00:5.50 |
| Min:Max | 0.0:8.2 | 1.0:9.5 | 0.0:8.8 | 0.0:9.8 |

TABLE 6-continued

Summary of change from baseline to Week 8 and 16 in the LBPI NRS score
(score range: 0 to 10) - MITT (Modified Intent To Treat set)

| Week | | Fasinumab | | |
|---|---|---|---|---|
| Average daily LBPI NRS score Change from Baseline | Placebo (N = 140) | 6 mg SC Q4W (N = 139) | 9 mg SC Q4W (N = 139) | 9 mg IV Q8W (N = 140) |
| Change from baseline to week 16 | | | | |
| n | 49 | 48 | 55 | 56 |
| Mean (SD) | −1.85 (2.130) | −2.14 (1.912) | −2.61 (1.975) | −2.52 (2.219) |
| Median | −1.23 | −2.06 | −2.60 | −2.75 |
| Q1:Q3 | −3.60:−0.20 | −3.55:−0.58 | −4.06:−1.06 | −3.98:−0.66 |
| Min:Max | −7.1:1.6 | −7.3:1.5 | −7.0:1.8 | −6.7:2.2 |
| LS Mean (SE) | −1.7 (0.23) | −2.0 (0.23) | −2.5 (0.22) | −2.4 (0.22) |
| 95% CI | (−2.19, −1.29) | (−2.46, −1.56) | (−2.90, −2.03) | (−2.83, −1.97) |
| Difference vs. Placebo LS Mean (SE) | | −0.3 (0.31) | −0.7 (0.30) | −0.7 (0.30) |
| 95% CI | | (−0.88, 0.34) | (−1.32, −0.12) | (−1.26, −0.07) |

Figure 5:
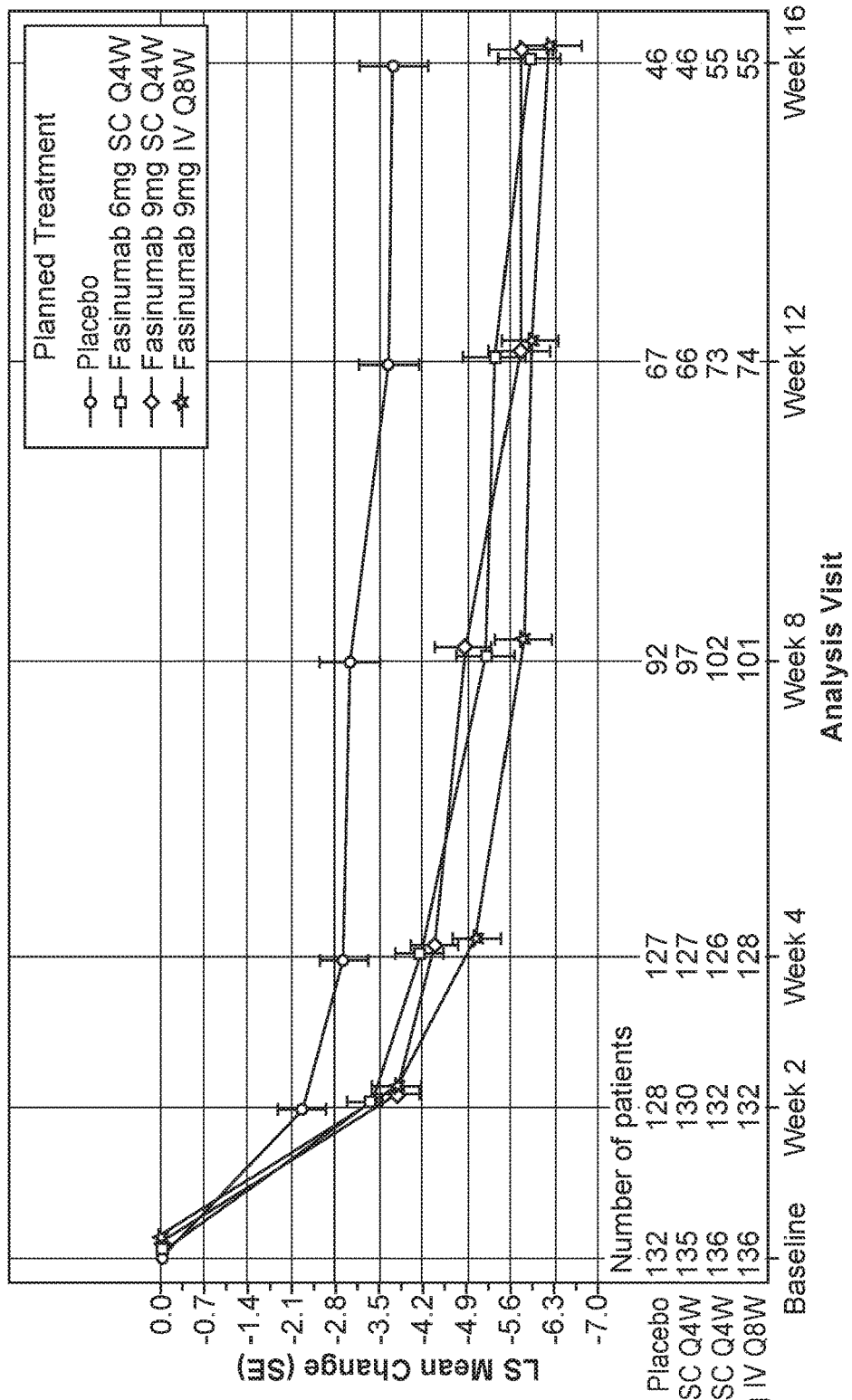
FIG. 5 shows the Change from Baseline to week 16 in the RMDQ Total Score by Visit: Least Squares Mean (+/−SE) (MITT).
Figure 6:
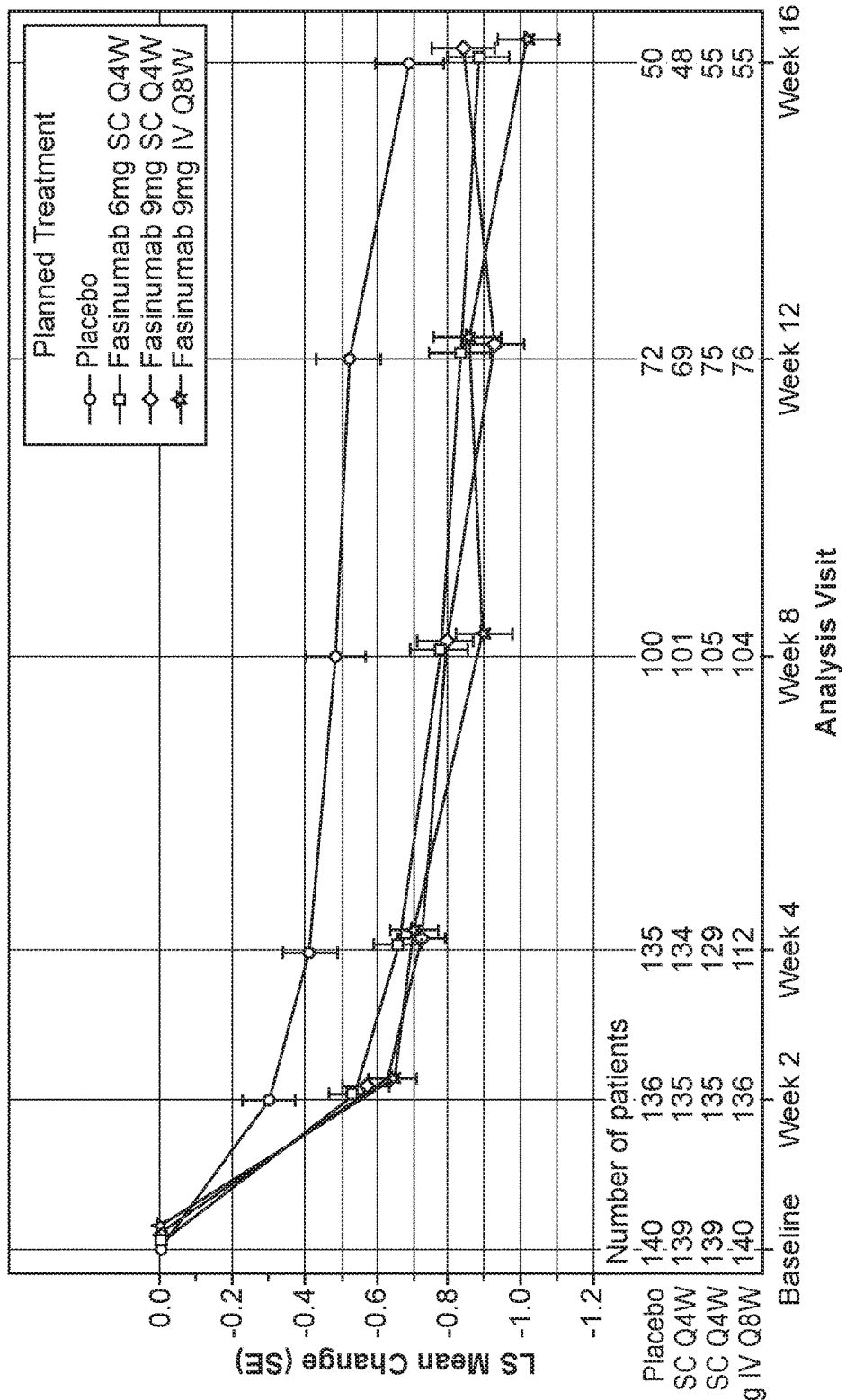
FIG. 6 shows the Change from Baseline to week 16 in the PGA of LBP by Visit: Least Squares Mean (+/−SE) (MITT).

SC = Subcutaneous; IV = Intravenous; Q4W = every 4 weeks; Q8W = every 8 weeks.
N = number of patients in the Modified Intent to Treat Set; n = number of patients within a specified category.
SD = Standard deviation; Min = Minimum; Max = Maximum; Q1 = First Quartile; Q3 = Third Quartile.
LS Mean = Least squares mean; SE = Standard error of the LS Mean; CI = Confidence Interval.
Analyses are based on MMRM model with baseline randomization strata, baseline score, treatment, visit, and treatment-by-visit interaction.
LBPI NRS = Lower Back Pain Intensity Numerical Rating Scale Secondary Efficacy Endpoints Secondary efficacy endpoints based on the Roland Morris Disability Questionnaire (RMDQ) and Patient Global Assessment (PGA) scores are summarized below in Tables 7 and 8 and in FIGS. 5 and 6, respectively. Greater improvement in the RMDQ total score at Week 16 was observed for all fasinumab doses compared with placebo. Greater improvement compared with placebo was observed as early as Week 2 for all doses and the treatment difference was maintained throughout the 16-week treatment period. Similar results were observed for the PGA at all timepoints for all doses compared to placebo.

TABLE 7

Summary of Change from Baseline to week 16
in the RMDQ Total Score by Visit - (MITT)

| Week | | Fasinumab | | |
|---|---|---|---|---|
| RMDQ Total Score Change from Baseline | Placebo (N = 140) | 6 mg SC Q4W (N = 139) | 9 mg SC Q4W (N = 139) | 9 mg IV Q8W (N = 140) |
| Baseline RMDQ Total Score | | | | |
| n | 132 | 135 | 136 | 136 |
| Mean (SD) | 10.87 (5.295) | 10.83 (5.157) | 10.73 (5.690) | 11.65 (5.257) |
| Median | 11.00 | 11.00 | 10.00 | 11.00 |
| Q1:Q3 | 7.00:15.00 | 7.00:14.00 | 6.00:15.00 | 8.00:15.00 |
| Min:Max | 1.0:23.0 | 1.0:23.0 | 1.0:24.0 | 2.0:23.0 |
| Week 16 RMDQ Total Score | | | | |
| n | 50 | 48 | 55 | 57 |
| Mean (SD) | 6.58 (5.599) | 5.08 (4.907) | 4.82 (4.583) | 5.04 (5.237) |
| Median | 4.50 | 4.00 | 4.00 | 3.00 |
| Q1:Q3 | 2.00:11.00 | 1.00:8.00 | 2.00:7.00 | 1.00:8.00 |
| Min:Max | 0.0:19.0 | 0.0:17.0 | 0.0:24.0 | 0.0:21.0 |
| Change from baseline to week 16 | | | | |
| n | 46 | 46 | 55 | 55 |
| Mean (SD) | −3.80 (4.465) | −6.04 (5.692) | −6.22 (4.740) | −6.64 (5.635) |
| Median | −3.00 | −5.50 | −6.00 | −6.00 |
| Q1:Q3 | −6.00:−1.00 | −10.00:−2.00 | −9.00:−2.00 | −11.00:−2.00 |
| Min:Max | −13.0:5.0 | −18.0:9.0 | −19.0:0.0 | −17.0:3.0 |
| LS Mean (SE) | −3.8 (0.54) | −6.0 (0.54) | −5.8 (0.51) | −6.3 (0.51) |

TABLE 7-continued

Summary of Change from Baseline to week 16 in the RMDQ Total Score by Visit - (MITT)

| Week RMDQ Total Score Change from Baseline | Placebo (N = 140) | Fasinumab | | |
|---|---|---|---|---|
| | | 6 mg SC Q4W (N = 139) | 9 mg SC Q4W (N = 139) | 9 mg IV Q8W (N = 140) |
| 95% CI | (−4.88, −2.76) | (−7.09, −4.97) | (−6.78, −4.76) | (−7.30, −5.28) |
| Difference vs. Placebo LS Mean (SE) | | −2.2 (0.73) | −2.0 (0.72) | −2.5 (0.72) |
| 95% CI | | (−3.65, −0.77) | (−3.36, −0.54) | (−3.88, −1.06) |

TABLE 8

Summary of Change from Baseline to week 16 in the PGA of LBP by Visit - (MITT)

| Week Patient Global Assessment Change from Baseline | Placebo (N = 140) | Fasinumab | | |
|---|---|---|---|---|
| | | 6 mg SC Q4W (N = 139) | 9 mg SC Q4W (N = 139) | 9 mg IV Q8W (N = 140) |
| Baseline Patient Global Assessment | | | | |
| n | 140 | 139 | 139 | 140 |
| Mean (SD) | 3.53 (0.734) | 3.47 (0.684) | 3.35 (0.796) | 3.42 (0.669) |
| Median | 4.00 | 3.00 | 3.00 | 3.00 |
| Q1:Q3 | 3.00:4.00 | 3.00:4.00 | 3.00:4.00 | 3.00:4.00 |
| Min:Max | 1.0:5.0 | 2.0:5.0 | 1.0:5.0 | 1.0:5.0 |
| Week 16 Patient Global Assessment | | | | |
| n | 50 | 48 | 55 | 57 |
| Mean (SD) | 2.80 (0.756) | 2.50 (0.899) | 2.53 (0.940) | 2.33 (0.951) |
| Median | 3.00 | 3.00 | 3.00 | 2.00 |
| Q1:Q3 | 2.00:3.00 | 2.00:3.00 | 2.00:3.00 | 2.00:3.00 |
| Min:Max | 1.0:4.0 | 1.0:4.0 | 1.0:4.0 | 1.0:4.0 |
| Change from baseline to week 16 | | | | |
| n | 50 | 48 | 55 | 57 |
| Mean (SD) | −0.66 (0.848) | −0.90 (1.057) | −0.84 (0.996) | −1.02 (0.855) |
| Median | −1.00 | −1.00 | −1.00 | −1.00 |
| Q1:Q3 | −1.00:0.00 | −1.50:0.00 | −1.00:0.00 | −2.00:0.00 |
| Min:Max | −3.0:1.0 | −3.0:2.0 | −4.0:1.0 | −3.0:1.0 |
| LS Mean (SE) | −0.7 (0.10) | −0.9 (0.10) | −0.8 (0.10) | −1.0 (0.09) |
| 95% CI | (−0.88, −0.49) | (−1.08, −0.69) | (−1.03, −0.65) | (−1.20, −0.83) |
| Difference vs. Placebo LS Mean (SE) | | −0.2 (0.14) | −0.1 (0.13) | −0.3 (0.13) |
| 95% CI | | (−0.46, 0.07) | (−0.41, 0.11) | (−0.59, −0.07) |

Exploratory Efficacy Endpoints

Table 9 summarizes response rates using various responder criteria by treatment groups. In general, patients in fasinumab groups were more likely to respond than placebo.

TABLE 9

Summary of Response Rates at Week 16 - FAS

| | | Fasinumab | | |
| --- | --- | --- | --- | --- |
| Variable | Placebo (N = 141) | 6 mg SC Q4W (N = 141) | 9 mg SC Q4W (N = 140) | 9 mg IV Q8W (N = 141) |
| RMDQ Total Score | | | | |
| >=30% reduction from baseline to week 16 | 48 (34.0%) | 74 (52.5%) | 83 (59.3%) | 71 (50.4%) |
| OR | | 2.125 | 2.905 | 1.999 |
| 95% CI | | (1.315, 3.434) | (1.769, 4.769) | (1.223, 3.266) |
| >=50% reduction from baseline to week 16 RMDQ Total Score | 32 (22.7%) | 55 (39.0%) | 66 (47.1%) | 61 (43.3%) |
| OR | | 2.159 | 3.110 | 2.663 |
| 95% CI | | (1.284, 3.631) | (1.835, 5.271) | (1.568, 4.522) |
| PGA of LBP Score | | | | |
| >=30% reduction from baseline to week 16 | 24 (17.0%) | 43 (30.5%) | 42 (30.0%) | 45 (31.9%) |
| OR | | 2.159 | 2.125 | 2.367 |
| 95% CI | | (1.223, 3.812) | (1.197, 3.775) | (1.327, 4.223) |
| >=50% reduction from baseline to week 16 | 10 (7.1%) | 18 (12.8%) | 20 (14.3%) | 23 (16.3%) |
| OR | | 1.934 | 2.255 | 2.738 |
| 95% CI | | (0.861, 4.347) | (1.004, 5.065) | (1.221, 6.137) |

SUMMARY AND CONCLUSIONS

At week 16, the improvement in the LBPI NRS score with all doses of fasinumab was greater compared with placebo. The results were similar to the results from the unplanned interim analysis.

Greater improvement in the LBPI NRS score was observed for all fasinumab doses compared to placebo as early as Week 2 through Week 16.

Greater improvements in the RMDQ and PGA were observed for all fasinumab doses compared to placebo as early as week 2 and maintained throughout the 16 week treatment period.

The most common TEAEs in fasinumab groups (≥3% in any fasinumab dose group) during the 16-week treatment period were arthralgia, nasopharyngitis, headache, paraesthesia, dizziness and hypoaesthesia.

There were no treatment-emergent SAEs occurring in more than one patient. There was also no dose dependency observed in the incidence of treatment emergent SAEs.

What is claimed is:

1. A method of treating a patient suffering from moderate to severe low back pain (LBP), wherein the low back pain is inadequately controlled by standard analgesic therapy, the method comprising:
   administering to the patient an initial dose of a pharmaceutical composition comprising 9 mg or 18 mg of an antibody that binds specifically to nerve growth factor (NGF) or an antigen binding fragment thereof, wherein the antibody or antigen-binding fragment comprises three heavy chain complementarity determining region (HCDR) sequences (HCDR1, HCDR2, HCDR3) comprising SEQ ID NOs: 4, 6 and 8, respectively, and three light chain complementarity determining (LCDR) sequences (LCDR1, LCDR2, LCDR3) comprising SEQ ID NOs: 12, 14 and 16, respectively;
   administering to the patient a plurality of secondary doses of the pharmaceutical composition comprising the NGF antagonist in an amount of 9 mg; and
   continuing the secondary doses to obtain an improvement in a pain-associated parameter.

2. The method of claim 1, wherein the low back pain is chronic, non-radicular back pain and wherein the patient exhibits a history of inadequate pain relief from, or is resistant, inadequately responsive, or intolerant to standard analgesic therapy.

3. The method of claim 1, wherein the patient is unwilling to take standard analgesic therapy, or wherein the standard analgesic therapy is inadvisable for administration to the patient due to safety and health risks and/or coupled with suboptimal efficacy.

4. The method of claim 3, wherein the standard analgesic therapy is inadvisable for administration to the patient due to a condition selected from the group consisting of medical contraindications, hypersensitivity to standard analgesic therapy, or excipients, use of a concomitant medication prohibited with standard analgesic therapy, increased risk of kidney damage, increased risk of liver damage, increased risk of gastrointestinal bleeding, increased risk of an allergic reaction and increased risk of developing drug dependence.

5. The method of claim 1, wherein the standard analgesic therapy is selected from the group consisting of paracetamol/acetaminophen, a non-steroidal anti-inflammatory (NSAID), and an opioid.

6. The method of claim 5, wherein the opioid is selected from the group consisting of hydrocodone, oxycodone, percocet, morphine, meperidine, hydromorphone, fentanyl, and methadone.

7. The method of claim 1, wherein the antibody or antigen-binding fragment thereof that binds specifically to NGF is administered to the patient at a frequency for the secondary doses of about every 4 weeks (Q4W), or every 8 weeks (Q8W).

8. The method of claim 7, wherein the antibody or antigen-binding fragment thereof that binds specifically to NGF is administered to the patient-at a frequency for the secondary doses of about every 4 weeks (Q4W).

9. The method of claim 7, wherein the antibody or antigen-binding fragment thereof that binds specifically to NGF is administered to the patient at a frequency for the secondary doses of about every 8 weeks (Q8W).

10. The method of claim 1, wherein the antibody or antigen-binding fragment is administered subcutaneously (SC), or intravenously (IV).

11. The method of 1, wherein the antibody comprises a heavy chain variable region (HCVR) comprising the amino acid sequence of SEQ ID NO:2 and a light chain variable region (LCVR) comprising the amino acid sequence of SEQ ID NO: 10.

12. The method of claim 1, wherein the patient, following administration of the pharmaceutical composition, exhibits an improvement in one or more pain-associated parameters selected from the group consisting of: (a) a change from baseline at week 16 in the average daily Low Back Pain Intensity (LBPI) Numerical Rating Scale (NRS) score; (b) a change from baseline at week 16 in the Roland Morris Disability Questionnaire (RMDQ) total score; (c) a change from baseline at week 16 in the Patient Global Assessment (PGA) of Low Back Pain (LBP) score; and (d) a change from baseline at week 2, 4, 8 and 12 in the average daily LBPI NRS score.

* * * * *